United States Patent
Cohn et al.

(10) Patent No.: US 6,818,428 B1
(45) Date of Patent: Nov. 16, 2004

(54) 3-PHOSPHOADENOSINE-5-PHOSPHOSULFATE (PAPS) SYNTHETASE PROTEINS AND METHODS FOR TREATING OSTEOARTHRITIC DISORDERS

(75) Inventors: Daniel H. Cohn, Santa Monica, CA (US); Muhammad Faiyaz-Ul-Haque, Islamabad (PK); Lily King, Los Angeles, CA (US); Deborah Krakow, Los Angeles, CA (US)

(73) Assignee: Cedars Sinai Medical Center, Los Angeles, CA (US)

( * ) Notice: Subject to any disclaimer, the term of this patent is extended or adjusted under 35 U.S.C. 154(b) by 242 days.

(21) Appl. No.: 09/898,165

(22) Filed: Jul. 2, 2001

Related U.S. Application Data

(62) Division of application No. 09/399,212, filed on Sep. 17, 1999, now abandoned.

(51) Int. Cl.[7] .......................... C12N 9/12; C12N 1/20; C12N 15/00; C07H 21/04; A61K 39/00

(52) U.S. Cl. ................. 435/194; 435/252.3; 435/320.1; 536/23.2; 424/192.1

(58) Field of Search .......................... 435/194, 252.3, 435/320.1; 536/23.2; 424/192.1; 530/387.1

(56) References Cited

U.S. PATENT DOCUMENTS

| | | | |
|---|---|---|---|
| 5,106,626 A | 4/1992 | Parsons et al. | 424/423 |
| 5,525,500 A | 6/1996 | Khandke et al. | 435/232 |
| 5,627,050 A | 5/1997 | Takeshita et al. | 435/69.1 |
| 5,750,651 A | 5/1998 | Oppermann et al. | 530/350 |
| 5,869,273 A | 2/1999 | Klock | 435/7.92 |
| 6,338,966 B1 * | 1/2002 | Falco et al. | 435/471 |

OTHER PUBLICATIONS

Fawell et al. PNAS., USA, 91 : 664–668 (1994).*
Franzon et al. Int. J. Biochem. & cell Biol. 31 : 613–626 (1999).*
Adams, T. E.., *Differential expression of growth hormone receptor messenger RNA from a second promoter*, Mol Cell Endocrinol, 108(1–2):23–33 (Feb. 27, 1995). Abstract Only.
Ahmad M. et al., *Distinct, autosomal recessive form of spondyloepimetaphyseal dysplasia segregating in an inbred Pakistani kindred*, Am J. Med Genet, 78(5):468–73, (Aug. 6, 1998).
Alexeev, V. et al., *Stable and inheritable changes in genotype and phenotype of albino melanocytes induced by an RNA–DNA oligonucleotide*, Nat Biotechnol, 16(13):1343–6 (Dec. 1998). Abstract Only.
Apte, S. S. et al., *Characterization of the mouse type X collagen gene*, Matrix 13(2):165–79 (Mar. 1993). Abstract Only.

Ballo, R. et al., *Multiple epiphyseal dysplasia, ribbing type: a novel point mutation in the COMP gene in a South African family*, Am J. Med Genet, 68(4):396–400 (Feb. 11, 1997). Abstract Only.
Beier, F., et al., *Localization of silencer and enhancer elements in the human type X collagen gene*, J Cell Biochem 66(2):210–8 (Aug. 1997). Abstract Only.
Boffa, M. B., *Characterization of the gene encoding human TAFI (thrombinactivable fibrinolysis inhibitor; plasma procarboxypeptidase B)*, Biochemsitry, 38(20):6547–58 (May 18, 1999). Abstract Only.
Bonaventure, J. et al., *Common mutations in the gene encoding fibroblast growth factor receptor 3 account for achondroplasia, hypochondroplasia and thanatophoric dysplasia*, Acta Paediatr Suppl, 417:33–8 (Oct. 1996). Abstract Only.
Briggs, M.D. et al., *Genetic mapping of a locus for multiple epiphyseal dysplasia (EDM2) to a region of chromosome 1 containing a type IX collagen gene*, Am J. Hum Genet, 55(4):678–84 (Oct. 1994). Abstract Only.
Briggs, M. D. et al., *Pseudoachondroplasia and multiple epiphyseal dysplasia due to mutations in the cartilage oligomeric matrix protein gene*, Nat Genet, 10(3):330–6 (Jul. 1995). Abstract Only.
Briggs, M. D. et al., *Diverse mutations in the gene for cartilage oligomeric matrix protein in the pseudoachondroplasia–multiple epiphyseal dysplasia disease spectrum*, Am J. Hum Genet, 62(2):311–9 (Feb. 1998). Abstract Only.
Chen, J. et al., *Hepatocyte nuclear factor 1 binds to and transactivates the human but not the rat CYP7A1 promoter*, Biochem Biophys Res Commun, 260(3):829–34 (Jul. 14, 1999). Abstract Only.

(List continued on next page.)

Primary Examiner—Tekchand Saidha
(74) Attorney, Agent, or Firm—Perkins Coie LLP

(57) ABSTRACT

Disclosed are isolated polynucleotides containing nucleic acid segments encoding human or murine ATP sulfurylase/APS kinase, also known as PAPS synthetase (PAPSS), particularly PAPSS2 and Papss2 proteins. Also disclosed are nucleic acid constructs, including vectors, probes, primers, and primer pairs containing novel PAPSS2 and Papss2 gene sequences. A genetically modified vertebrate cell containing a nucleic acid construct of the present invention and a non-human vertebrate comprising the cell are also disclosed. Based on the present PAPSS2-specific polynucleotides and nucleic acid constructs, are genetic testing kits and methods for diagnosing spondyloepimetaphyseal dysplasia (SEMD) in a human subject, of identifying a human carrier of an heritable allele associated with SEMD, and of gene therapy or protein therapy for treating a human subject having an osteoarthritic disorder, which is caused or aggravated by deficient enzymatic sulfation activity. Also disclosed is a protein therapy method for treating a human subject having an osteoarthritic disorder caused or aggravated by deficient enzymatic sulfation activity that employs an inventive PAPSS2 fusion protein. Also disclosed are an isolated antibody or antibody fragment that selectively binds a PAPSS2 or Papss2 protein.

5 Claims, 4 Drawing Sheets

OTHER PUBLICATIONS

Chen, X. L. et al., *Analysis of a 762–bp Proximal Leptin Promoter to Drive and Control Regulation of Transgene Expression of Growth Hormone Receptor in Mice*, Biochem Biophys Res Commun, 262(1):187–192 (Aug. 19, 1999). Abstract Only.

Cole–Strauss, A. et al., *Correction of the mutation responsible for sickle cell anemia by an RNA–DNA oligonucleotide*, Science, 273(5280):1386–9 (Sep. 6, 1996). Abstract Only.

Cole–Strauss, A. et al., *Targeted gene repair directed by the chimeric RNA/DNA oligonucleotide in a mammalian cell–free extract*, Nucleic Acids Res, 27(5):1323–30 (Mar. 1, 1999). Abstract Only.

Deyrup, A. T. et al., *Deletion and site–directed mutagenesis of the ATP–binding motif (P–loop) in the bifunctional murine ATP–sulfurylase/adenosine 5'–phosphosulfate kinase enzyme*, J Biol Chem, 273(16):9450–6 (Apr. 17, 1998).

Dharmavaram, R. M., et al., *Detection and characterization of Sp1 binding activity in human chondrocytes and its alterations during chondrocyte dedifferentiation*, J. Biol Chem, 272(43):26918–25 (Oct. 24, 1997). Abstract Only.

Faiyaz ul Haque, Muhammad et al., *Mutations in orthologous genes in human spondyloepimetaphyseal dysplasia and the brachymorphic mouse*, Nature Genetics, vol. 20, pp. 157–162. (Oct. 1998).

Figuera, L. E. et al., *Spondyloepimetaphyseal dysplasia (SEMD) Shohat type*, Am J. Med Genet, 51(3):213–5 (Jul. 1994). Abstract Only.

Ganguly, A., et al., *Targeted insertions of two exogenous collagen genes into both alleles of their endogenous loci in cultured human cells: the insertions are directed by relatively short fragments containing the promoters and the 5' ends of the genes*, Proc Natl Acad Sci USA, 91(15):7365–9 (Jul. 19, 1994). Abstract Only.

Gertner, J. M. et al., *Linkage studies of a Missouri kindred with autosomoal dominant spondyloepimetaphyseal dysplasia (SEMD) indicate genetic heterogeneity*, J Bone Miner Res, 12(8):1204–9 (Aug. 12, 1997). Abstract Only.

Girard, J. P. et al., *Biosynthesis of sulfated L–selectin ligands in human high endothelial venules (HEV)*, GlycoImmunology, 2:55–62 (1998).

Girard, J. P. et al., *Sulfation in high endothelial venules: cloning and expression of the human PAPS synthetase*, FASEB, 12(7):603–12 (May 1998).

Ikegawa, S. et al., *Novel and recurrent COMP (cartilage oligomeric matrix protein) mutations in pseudoachondroplasia and multiple epiphyseal dysplasia*, Hum Genet, 103(6):633–8 (Dec. 1998). Abstract Only.

Jacenko, O. et al., *Transgenic mouse models in studies of skeletal disorders*, J Rheumatol Suppl 43:39–41 (Feb. 1995). Abstract Only.

Jiang, H. et al., *Isolation and characterization of a novel promoter for the bovine growth hormone receptor gene*, J Biol Chem, 274(12):7893–900 (Mar. 19, 1999). Abstract Only.

Kanai, Y et al., *Structural and functional characterization of the mouse Sox9 promoter: implications for campomelic dysplasia*, Hum Mol Genet, 8(4):691–6 (Apr. 1999). Abstract Only.

Kant, S. G. et al., *Acromesomelic dysplasia Maroteau type maps to human chromosome 9*, Am J Hum Genet, 63(1):155–62 (Jul. 1998). Abstract Only.

Kanzler, S. et al., *TGF–beta1 in liver fibrosis: an inducible transgenic mouse model to study liver fibrogenesis*, Am J Physiol, 276(4 Pt 1):G1059–68 (Apr. 1999). Abstract Only.

Kren, B. T. et al., *Gene repair using chimeric RNA/DNA oligonucleotides*, Semin Liver Dis, 19(1):93–104 (1999). Abstract Only.

Kurima, K. et al., *A member of a family of sulfate–activating enzymes causes murine brachymorphism*, Proc Natl Acad Sci USA, 95(15):8681–5 (Jul. 21, 1998).

Lee, B. et al., *Identification of the molecular defect in a family with spondyloepiphyseal dysplasia*, Science, 244(4907):978–80 (May 26, 1989). Abstract Only.

Lefebvre, V., et al., *An 18–base–pair sequence in the mouse proalpha1(II) collagen gene is sufficient for expression in cartilage and binds nuclear proteins that are selectively expressed in chondrocytes*, Mol Cell Biol, 16(8):4512–23 (Aug. 16, 1996). Abstract Only.

Li, H. et al., *The isolation and characterization of cDNA encloding the mouse bifunctional ATP sulfurylase–adenosine 5'–phosphosulfate kinase*, J Biol Chem, 270(49):29453–9 (Dec. 8, 1995).

Li, Y et al., *Murine models of human genetic skeletal disorders*, Matrix Biol, 16(2):49–52. (May 1997). Abstract Only.

Lyle, S. et al., *Rat chondrosarcoma ATP sulfurylase and adenosine 5'–phosphosulfate kinase reside on a single bifunctional protein*, Biochemsitry, 33(19):5920–5 (May 17, 1994). Abstract Only.

Lyle, S. et al., *Intermediate channeling between ATP sulfurylase and adenosine 5'–phosphosulfate kinase from rat chondrasarcoma*, Biochemistry, 33(22):6822–7 (Jun. 1994). Abstract Only.

Masuya, Y. et al., *MAP kinase–independent induction of proto–oncogene c–fos mRNA by hemin in human cells*, Biochem Biophys Res Commun, 260(1):289–95 (Jun. 24, 1999). Abstract Only.

Meton, I et al., *Growth hormone induces insulin–like growth factor–I gene transcription by a synergistic action of STAT5 and HNF–1alpha*, FEBS Lett, 444(203):155–59 (Feb. 12, 1999). Abstract Only.

Mukhopadhyay, K., et al., *Use of a new rat chondrosarcoma cell line to delineate a 119–base pair chondrocyte–specific enhancer element and to define active promoter segments in the mouse pro–alpha I(II) collagen gene*, J. Biol Chem, 270(46):27711–9 (Nov. 17, 1995). Abstract Only.

Newberry, E. P. et al., *The RRM Domain of MINT, a Novel Msx2 Binding Protein, Recognizes and Regulates the Rat Osteocalcin Promoter*, Biochemistry, 38(33): 10678–10690 (Aug. 17, 1999). Abstract Only.

Nitta, M. et al., *CPF: an orphan nuclear receptor that regulates liver–specific expression of the human cholesterol 7alpha–hydroxylase gene*, Proc Natl Acad Sci USA, 96(12):6660–5 (Jun. 8, 1999). Abstract Only.

Pastore, L. et al., *Use of a liver–specific promoter reduces immune response to the transgene in adenoviral vectors*, Hum Gene Ther, 10(11):1773–81 (Jul. 20, 1999). Abstract Only.

Rosenthal, e. et al., *A multifunctional Urechis caupo protein, PAPS synthetase, has both ATP sulfurylase and APS kinase activities*, Gene, 165(2):243–8 (Nov. 20, 1995). Abstract Only.

Schwarze, Steven R. et al., *In vivo Protein Transduction: Delivery of a Biologically Active Protein Into the Mouse*, Science, vol. 285, pp. 1569–1572 (Sep. 3, 1999).

Schwartz, N. B. et al., *Sulfate activation and transport in mammals: system components and mechanisms*, Chem Biol Interact, 109(1–3):143–51 (Feb. 20, 1998).

Seghatoleslami, M. R., et al.., *Differential regulation of COL2A1 expression in developing and mature chondrocytes*, Matrix Biol, 14(9):753–64 (Dec. 1995). Abstract Only.

Shohat, M. et al., *New form of spondyloepimetaphyseal dysplasia (SEMD) in Jewish family of Iraqi origin*, Am J. Med Genet, 46(4):358–62 (Jun. 1, 1993). Abstract Only.

Sokolov, B. P., et al., *Tissue–specific expression of the gene for type I procollagen (COL1A1) in transgenic mice. Only 476 base pairs of the promoter are required if collagen genes are used as reporters*, J. Biol Chem, 270(16):9622–9 (Apr. 21, 1995). Abstract Only.

Steimberg, N. et al., *SV40 large T antigen expression driven by col2a1 regulatory sequences immortalizes articular chondrocytes but does not allow stabilization of type II collagen expression*, Exp Cell Res, 249(2):248–59 (Jun. 15, 1999). Abstract Only.

Strauss, Evelyn, *Introducing Proteins Into the Body s Cells*, Science, vol. 285, pp. 1466–1467 (Sep. 3, 1999).

Sugahara, K. et al., *Defect in 3'–phosphoadenosine 5'–phosphosulfate formation in brachymorphic mice*, Proc Natl Acad Sci USA, 76(12):6615–8 (Dec. 1979). Abstract Only.

Superti–Furga, A. et al., *A chondrodysplasia family produced by mutations in the diastrophic dysplasia sulfate transporter gene: genotype/phenotype correlations*, Am J Med Genet, 63(1):144–7 (May 1996). Abstract Only.

Tewari, D. S., *Characterization of the promoter region and 3' end of the human insulin receptor gene*, J Biol Chem, 264(27):16238–45 (Sep. 25, 1989). Abstract Only.

Thomas, J. T., et al., *Sequence comparison of three mammalian type–X collagen promoters and preliminary functional analysis of the human promoter*, Gene 160(2):291–6 (Jul. 28, 1995). Abstract Only.

Thomas, J. T. et al., *A human chondrodysplasia due to a mutation in a TGF–beta superfamily member*, Nat Genet, 12(3):315–7 (Mar. 1996). Abstract Only.

Truter, S. et al, *Pro–alpha 2(V) collagen gene; pairwise analysis of the amino–propeptide coding domain, and cross–species comparison of the promoter sequence*, Connect Tissue Res, 29(1):51–9 (1993). Abstract Only.

Venkatachalam, K. V. et al. *Molecular cloning, expression, and characterization of human bifunctional 3'–phosphoadenosine 5'–phosphosulfate synthase and its functional domains*, J. Biol Chem, 273(30):19311–20 (Jul. 24, 1998).

Venkatachalam, K. V. et al., *Site–selected mutagenesis of a conserved nucleotide binding HXGH motif located in the ATP sulfurylase domain of human bifunctional 3'–phosphoadenosine 5'–phosphosulfate synthase*, J Biol Chem, 274(5):2601–4 (Jan. 29, 1999).

Vikkula, M., et al., *Structural analysis of the regulatory elements of the tyupe–II procollagen gene. Conservation of promoter and first intron sequences between human and mouse*, Biochem J, 285(Pt 1):287–94 (Jul. 1, 1992). Abstract Only.

Vincent, J. et al., *Oligonucleotides as short as 7–mers can be used for PCR amplification*, DNA Cell Biol, 13(1):75–82 (Jan. 1994). Abstract Only.

Wallis, G. A., *Cartilage disorders. The importance of being sulphated*, Curr Biol, 5(3):225–7 (Mar. 1, 1995).

Wilcox, D. A. et al., *Integrin alphaIIb promoter–targeted expression of gene products in megakaryocytes derived from retrovirustransduced human hematopoietic cells*, Proc Natl Acad Sci USA, 96(17):9654–9659 (Aug. 17, 1999). Abstract Only.

Xiang, Y. et al., *Targeted gene conversion in a mammalian CD34=–enriched cell population using a chimneric RNA/DNA oligonucleotide*, J Mol Med, 75(11–12):829–35 (Nov.–Dec. 1997). Abstract Only.

Xie, W.F. et al. *Trans–activation of the mouse cartilage–derived retinoic acid–sensitive protein gene by Sox9*, J Bone Miner Res, 14(5):757–63 (May 1999). Abstract Only.

Yamada, K. et al. *The histochemistry of complex cabohydrates in certain organs of homozygous brachymorphic (bm/bm) mice*, Histochem J, 16(6):587–99 (Jun. 1984). Abstract Only.

Yanagisawa, K. et al., *cDNA cloning, expression, and characterizaiton of the human bifunctional ATP sulfuryklase/adenosine 5'–phophosulfate kinase enzyme*, Biosci Biotechnol Biochem, 62(5):1037–40 (May 1998). Abstract Only.

Yoon, K. et al., *Targeted gene correction of episomal DNA in mammalian cells mediated by a chimeric RNA.DNA oligonucleotide*, Proc Natl Acad Sci USA, 93(5):2071–6 (Mar. 1996). Abstract Only.

Zhou, G., et al., *A 182 bp fragment of the mouse pro alpha I(II) collagen gene is sufficient to direct chondrocyte expression in transgenic mice*, J Cell Sci, 108(Pt 12):3677–84 (Dec. 1995). Abstract Only.

Zou, I et al., *Isolation of a liver–specific promoter for human growth hormone receptor gene*, Endocrinology, 138(4):1771–4 (Apr. 1997). Abstract Only.

Zhou, G., et al., *Three high mobility group–like sequences within a 48–base pair enhancer of the Col2a1 gene are required for cartilage–specific expression in vivo*, J. Biol Chem, 273(24):14989–97 (Jun. 12, 1998). Abstract Only.

\* cited by examiner

```
normal  ...GAT CCC AAG TCA ACC ATT... (SEQ ID NO:30)
           D   P   K   S   T   I (SEQ ID NO:31)
                           ↓
SEMD    ...GAT CCC AAG TAA ACC ATT... (SEQ ID NO:32)
           D   P   K   X       (SEQ ID NO:33)
``` ns and Methods for Treating Osteoarthritic Disorders

SEQUENCE LISTING

<160> NUMBER OF SEQ ID NOS: 33

<210> SEQ ID NO 1
<211> LENGTH: 2014
<212> TYPE: DNA
<213> ORGANISM: Homo sapiens

<400> SEQUENCE: 1

```
ctgctgccgc cgccgccgcc gccgtccctg cgtccttcgg tctctgctcc cgggacccgg      60
ctccgccgca gccagccagc atgtcgggga tcaagaagca aaagacggag aaccagcaga     120
aatccaccaa tgtagtctat caggcccacc atgtgagcag gaataagaga gggcaagtgg     180
ttggaacaag gggtgggttc cgaggatgta ccgtgtggct aacaggtctc tctggtgctg     240
gaaaaacaac gataagtttt gccctggagg agtaccttgt ctcccatgcc atcccttgtt     300
actccctgga tggggacaat gtccgtcatg ccttaacag aaatctcgga ttctctcctg      360
gggacagaga ggaaaatatc cgccggattg ctgaggtggc taagctgttt gctgatgctg     420
gtctggtctg cattaccagc tttatttctc cattcgcaaa ggatcgtgag aatgcccgca     480
aaatacatga atcagcaggg ctgccattct ttgaaatatt tgtagatgca cctctaaata     540
tttgtgaaag cagagacgta aaggcctct ataaagggc cagagctggg gagattaaag       600
gatttacagg tattgattct gattatgaga acctgaaac tcctgagcgt gtgcttaaaa      660
ccaatttgtc cacagtgagt gactgtgtcc accaggtagt ggaacttctg caagagcaga     720
acattgtacc ctatactata atcaaagata tccacgaact ctttgtgccg gaaaacaaac     780
ttgaccacgt ccgagctgag gctgaaactc tcccttcatt atcaattact aagctggatc     840
tccagtgggt ccaggttttg agcgaaggct gggccactcc cctcaaaggt ttcatgcggg     900
agaaggagta cttacaggtt atgcactttg acaccctgct agatgatggc gtgatcaaca     960
tgagcatccc cattgtactg cccgtctctg cagaggataa gacacggctg aagggtgca    1020
gcaagtttgt cctggcacat ggtggacgga gggtagctat cttacgagac gctgaattct    1080
atgaacacag aaaagaggaa cgctgttccc gtgtttgggg gacaacatgt acaaaacacc    1140
cccatatcaa aatggtgatg gaaagtgggg actggctggt tggtggagac cttcaggtgc    1200
tggagaaaat aagatggaat gatgggctgg accaataccg tctgacacct ctggagctca    1260
aacagaaatg taaagaaatg aatgctgatg cggtgtttgc attccagttg cgcaatcctg    1320
tccacaatgg ccatgccctg ttgatgcagg acacctgccg caggctccta gagaggggct    1380
acaagcaccc ggtcctccta ctacaccctc tgggcggctg gaccaaggat gacgatgtgc    1440
ctctagactg gcggatgaag cagcacgcgg ctgtgctcga ggaagggtc ctggatccca     1500
agtcaaccat tgttgccatc tttccgtctc ccatgttata tgctggcccc acagaggtcc    1560
agtggcactg caggtcccgg atgattgcgg gtgccaattt ctacattgtg gggagggacc    1620
ctgcaggaat gccccatcct gaaaccaaga aggatctgta tgaacccact catggggca    1680
aggtcttgag catggcccct ggcctcacct ctgtggaaat cattccattc gagtggctg     1740
cctacaacaa agccaaaaaa gccatggact tctatgatcc agcaaggcac aatgagtttg    1800
acttcatctc aggaactcga atgaggaagc tcgcccggga aggagagaat cccccagatg    1860
gcttcatggc cccaaagca tggaaggtcc tgacagatta ttacaggtcc ctggagaaga     1920
actaagcctt tgggtccaga gtttctttct gaagtgctct ttgattacct tttctatttt    1980
tatgattaga tgctttgtat taaattgctt ctca                                2014
```

<210> SEQ ID NO 2
<211> LENGTH: 2000
<212> TYPE: DNA
<213> ORGANISM: Mus musculus

<400> SEQUENCE: 2

```
gtattctcaa catcagatat catgtcttgg aggaagttac ctaaactctg aagaattatc      60
```

-continued

```
atgtctgcaa atttcaaaat gaaccataaa agagaccagc aaaaatccac caatgtggtc      120
taccaggccc atcatgtgag caggaacaag agaggacaag tggttggaac caggggagga      180
ttccgaggat gtaccgtgtg ctaacaggt ctctctggtg ctgggaaaac aaccataagc       240
tttgctttgg aagagtacct tgtatctcac gccatcccat gttactccct ggatggggac      300
aatgtccgtc atggccttaa taagaacctg ggattctctg ccggggaccg agaagagaat      360
atccgccgga tcgcggaggt ggccaagctc tttgccgacg ccggcctggt ttgcatcacc      420
agctttatct ctccttttgc aaaggatcgt gagaatgccc gaaaaatcca cgaatcagca      480
ggactcccgt tctttgagat ctttgtagat gcgcctttaa atatctgtga aagccgagac      540
gtaaaaggac tctacaaacg agcccgagca ggagagatta agggtttac aggcatcgat       600 tctgactatg agaaacctga aactccagag tgtgtgctga agaccaactt gtcttcagta      660
agcgactgtg tgcaacaggt ggtggaactt ttgcaggagc agaacattgt accccacacc      720
accatcaaag gcatccacga actctttgtg ccagaaaaca aagtcgatca aatccgagct      780
gaggcagaga ctctcccatc actaccaatt accaagctgg atctgcagtg ggtgcagatt      840
ctgagtgaag gctgggccac tcccctcaaa ggctttatgc gggagaagga atacttgcaa      900
actctacact tcgacactct actggacgat ggagtcatca acatgagtat tcccattgta      960
ttgcccgttt ctgcggatga caaggcacgg ctcgaagggt gcagcaaatt tgccttgatg     1020
tacgaaggtc ggagggtcgc tctattacag gaccctgaat tctatgagca taggaaagag     1080
gagcgttgtt ctcgtgtgtg gggaacagcc actgcaaagc accccatat caaaatggtg      1140 atggaaagtg gggactggct tgttggtgga gacctacagg tgctagagag aataaggtgg     1200
gacgatgggc tggaccaata ccgccttacg cctctggaac tcaaacagaa gtgtaaagac     1260
atgaatgctg atgccgtgtt tgcattccag ttgcgcaatc ctgtccacaa tggtcatgcc     1320
ctcctgatgc aggacacccg ccgcaggctc ctggagaggg gttacaagca cccagtcctc     1380
ctgctccacc ctcttggggg ctggaccaag gacgatgacg tacctctgga atggaggatg     1440
aaacagcatg cagctgtact ggaggaaagg gtcctggatc ccaagtcaac tattgttgcc     1500
atctttccat ctcctatgtt atacgctggt cccacagagg tccagtggca ttgcagatgc     1560
cggatgattg caggagccaa tttctacatt gtgggtaggg atcccgcagg aatgccccat     1620
cctgagacaa agaaagacct atatgaaccc acccacgggg gcaaggtctt gagtatggcc     1680
cctggcctta cctctgtgga aataattccg ttccgagtgg ctgcctacaa taaaattaaa     1740
aaggccatgg acttttatga tccagcaagg cacgaggagt ttgacttcat ctcaggaact     1800
cgcatgagga agctcgcccg ggaaggagaa gatcccccag atggcttcat ggccccgaaa     1860
gcgtggaaag tgttgacaga ttactacagg tctctggaga agaccaacta ggtgctcctg     1920
gctctggctt cttcctcaag tgctctctga cgattttttt tttctatttt tgtgatttag     1980
ctgctctgta tccaattgca                                                  2000
```

<210> SEQ ID NO 3
<211> LENGTH: 20
<212> TYPE: DNA
<213> ORGANISM: Homo sapiens

<400> SEQUENCE: 3
tggaccaagg atgacgatgt                                                      20

<210> SEQ ID NO 4
<211> LENGTH: 20

```
<212> TYPE: DNA
<213> ORGANISM: Homo sapiens

<400> SEQUENCE: 4
cggaaagatg gcaacaatgg                                                  20

<210> SEQ ID NO 5
<211> LENGTH: 20
<212> TYPE: DNA
<213> ORGANISM: Homo sapiens

<400> SEQUENCE: 5
ctggtgctgg aaaaacaacg                                                  20

<210> SEQ ID NO 6
<211> LENGTH: 22
<212> TYPE: DNA
<213> ORGANISM: Homo sapiens

<400> SEQUENCE: 6
tgcgaatgga gaaataaagc tg                                               22

<210> SEQ ID NO 7
<211> LENGTH: 615
<212> TYPE: PRT
<213> ORGANISM: Homo sapiens

<400> SEQUENCE: 7
```

Met Ser Gly Ile Lys Lys Gln Lys Thr Glu Asn Gln Gln Lys Ser Thr
 1               5                  10                  15

Asn Val Val Tyr Gln Ala His His Val Ser Arg Asn Lys Arg Gly Gln
            20                  25                  30

Val Val Gly Thr Arg Gly Gly Phe Arg Gly Cys Thr Val Trp Leu Thr
        35                  40                  45

Gly Leu Ser Gly Ala Gly Lys Thr Thr Ile Ser Phe Ala Leu Glu Glu
    50                  55                  60

Tyr Leu Val Ser His Ala Ile Pro Cys Tyr Ser Leu Asp Gly Asp Asn
65                  70                  75                  80

Val Arg His Gly Leu Asn Arg Asn Leu Gly Phe Ser Pro Gly Asp Arg
                85                  90                  95

Glu Glu Asn Ile Arg Arg Ile Ala Glu Val Ala Lys Leu Phe Ala Asp
            100                 105                 110

Ala Gly Leu Val Cys Ile Thr Ser Phe Ile Ser Pro Phe Ala Lys Asp
        115                 120                 125

Arg Glu Asn Ala Arg Lys Ile His Glu Ser Ala Gly Leu Pro Phe Phe
    130                 135                 140

Glu Ile Phe Val Asp Ala Pro Leu Asn Ile Cys Glu Ser Arg Asp Val
145                 150                 155                 160

Lys Gly Leu Tyr Lys Arg Ala Arg Ala Gly Glu Ile Lys Gly Phe Thr
                165                 170                 175

Gly Ile Asp Ser Asp Tyr Glu Lys Pro Glu Thr Pro Glu Arg Val Leu
            180                 185                 190

Lys Thr Asn Leu Ser Thr Val Ser Asp Cys Val His Gln Val Val Glu
        195                 200                 205

Leu Leu Gln Glu Gln Asn Ile Val Pro Tyr Thr Ile Lys Asp Ile
    210                 215                 220

His Glu Leu Phe Val Pro Glu Asn Lys Leu Asp His Val Arg Ala Glu
225                 230                 235                 240

-continued

```
Ala Glu Thr Leu Pro Ser Leu Ser Ile Thr Lys Leu Asp Leu Gln Trp
                245                 250                 255

Val Gln Val Leu Ser Glu Gly Trp Ala Thr Pro Leu Lys Gly Phe Met
            260                 265                 270

Arg Glu Lys Glu Tyr Leu Gln Val Met His Phe Asp Thr Leu Leu Asp
        275                 280                 285

Asp Gly Val Ile Asn Met Ser Ile Pro Ile Val Leu Pro Val Ser Ala
    290                 295                 300

Glu Asp Lys Thr Arg Leu Glu Gly Cys Ser Lys Phe Val Leu Ala His
305                 310                 315                 320

Gly Gly Arg Arg Val Ala Ile Leu Arg Asp Ala Glu Phe Tyr Glu His
                325                 330                 335

Arg Lys Glu Glu Arg Cys Ser Arg Val Trp Gly Thr Thr Cys Thr Lys
            340                 345                 350

His Pro His Ile Lys Met Val Met Glu Ser Gly Asp Trp Leu Val Gly
        355                 360                 365

Gly Asp Leu Gln Val Leu Glu Lys Ile Arg Trp Asn Asp Gly Leu Asp
    370                 375                 380

Gln Tyr Arg Leu Thr Pro Leu Glu Leu Lys Gln Lys Cys Lys Glu Met
385                 390                 395                 400

Asn Ala Asp Ala Val Phe Ala Phe Gln Leu Arg Asn Pro Val His Asn
                405                 410                 415

Gly His Ala Leu Leu Met Gln Asp Thr Cys Arg Arg Leu Leu Glu Arg
            420                 425                 430

Gly Tyr Lys His Pro Val Leu Leu Leu His Pro Leu Gly Gly Trp Thr
        435                 440                 445

Lys Asp Asp Val Pro Leu Asp Trp Arg Met Lys Gln His Ala Ala
    450                 455                 460

Val Leu Glu Glu Gly Val Leu Asp Pro Lys Ser Thr Ile Val Ala Ile
465                 470                 475                 480

Phe Pro Ser Pro Met Leu Tyr Ala Gly Pro Thr Glu Val Gln Trp His
                485                 490                 495

Cys Arg Ser Arg Met Ile Ala Gly Ala Asn Phe Tyr Ile Val Gly Arg
            500                 505                 510

Asp Pro Ala Gly Met Pro His Pro Glu Thr Lys Lys Asp Leu Tyr Glu
        515                 520                 525

Pro Thr His Gly Gly Lys Val Leu Ser Met Ala Pro Gly Leu Thr Ser
    530                 535                 540

Val Glu Ile Ile Pro Phe Arg Val Ala Ala Tyr Asn Lys Ala Lys Lys
545                 550                 555                 560

Ala Met Asp Phe Tyr Asp Pro Ala Arg His Asn Glu Phe Asp Phe Ile
                565                 570                 575

Ser Gly Thr Arg Met Arg Lys Leu Ala Arg Glu Gly Glu Asn Pro Pro
            580                 585                 590

Asp Gly Phe Met Ala Pro Lys Ala Trp Lys Val Leu Thr Asp Tyr Tyr
        595                 600                 605

Arg Ser Glu Met Asp Lys Asn
    610                 615

<210> SEQ ID NO 8
<211> LENGTH: 617
<212> TYPE: PRT
<213> ORGANISM: Mus musculus
```

<400> SEQUENCE: 8

```
Met Ser Ala Asn Phe Lys Met Asn His Lys Arg Asp Gln Gln Lys Ser
  1               5                  10                  15

Thr Asn Val Val Tyr Gln Ala His His Val Ser Arg Asn Lys Arg Gly
             20                  25                  30

Gln Val Val Gly Thr Arg Gly Gly Phe Arg Gly Cys Thr Val Trp Leu
         35                  40                  45

Thr Gly Leu Ser Gly Ala Gly Lys Thr Thr Ile Ser Phe Ala Leu Glu
     50                  55                  60

Glu Tyr Leu Val Ser His Ala Ile Pro Cys Tyr Ser Leu Asp Gly Asp
 65                  70                  75                  80

Asn Val Arg His Gly Leu Asn Lys Asn Leu Gly Phe Ser Ala Gly Asp
                 85                  90                  95

Arg Glu Glu Asn Ile Arg Arg Ile Ala Glu Val Ala Lys Leu Phe Ala
            100                 105                 110

Asp Ala Gly Leu Val Cys Ile Thr Ser Phe Ile Ser Pro Phe Ala Lys
        115                 120                 125

Asp Arg Glu Asn Ala Arg Lys Ile His Glu Ser Ala Gly Leu Pro Phe
    130                 135                 140

Phe Glu Ile Phe Val Asp Ala Pro Leu Asn Ile Cys Glu Ser Arg Asp
145                 150                 155                 160

Val Lys Gly Leu Tyr Lys Arg Ala Arg Ala Gly Glu Ile Lys Gly Phe
                165                 170                 175

Thr Gly Ile Asp Ser Asp Tyr Glu Lys Pro Glu Thr Pro Glu Cys Val
            180                 185                 190

Leu Lys Thr Asn Leu Ser Ser Val Ser Asp Cys Val Gln Gln Val Val
        195                 200                 205

Glu Leu Leu Gln Glu Gln Asn Ile Val Pro His Thr Thr Ile Lys Gly
    210                 215                 220

Ile His Glu Leu Phe Val Pro Glu Asn Lys Val Asp Gln Ile Arg Ala
225                 230                 235                 240

Glu Ala Glu Thr Leu Pro Ser Leu Pro Ile Thr Lys Leu Asp Leu Gln
                245                 250                 255

Trp Val Gln Ile Leu Ser Glu Gly Trp Ala Thr Pro Leu Lys Gly Phe
            260                 265                 270

Met Arg Glu Lys Glu Tyr Leu Gln Thr Leu His Phe Asp Thr Leu Leu
        275                 280                 285

Asp Asp Gly Val Ile Asn Met Ser Ile Pro Ile Val Leu Pro Val Ser
    290                 295                 300

Ala Asp Asp Lys Ala Arg Leu Glu Gly Cys Ser Lys Phe Ala Leu Met
305                 310                 315                 320

Tyr Glu Gly Arg Arg Val Ala Leu Leu Gln Asp Pro Glu Phe Tyr Glu
                325                 330                 335

His Arg Lys Glu Glu Arg Cys Ser Arg Val Trp Gly Thr Ala Thr Ala
        340                 345                 350

Lys His Pro His Ile Lys Met Val Met Glu Ser Gly Asp Trp Leu Val
    355                 360                 365

Gly Gly Asp Leu Gln Val Leu Glu Arg Ile Arg Trp Asp Asp Gly Leu
370                 375                 380

Asp Gln Tyr Arg Leu Thr Pro Leu Glu Leu Lys Gln Lys Cys Lys Asp
385                 390                 395                 400

Met Asn Ala Asp Ala Val Phe Ala Phe Gln Leu Arg Asn Pro Val His
                405                 410                 415
```

```
Asn Gly His Ala Leu Leu Met Gln Asp Thr Arg Arg Leu Leu Glu
            420                 425                 430
Arg Gly Tyr Lys His Pro Val Leu Leu His Pro Leu Gly Gly Trp
        435                 440                 445
Thr Lys Asp Asp Val Pro Leu Glu Trp Arg Met Lys Gln His Ala
    450                 455                 460
Ala Val Leu Glu Glu Arg Val Leu Asp Pro Lys Ser Thr Ile Val Ala
465                 470                 475                 480
Ile Phe Pro Ser Pro Met Leu Tyr Ala Gly Pro Thr Glu Val Gln Trp
                485                 490                 495
His Cys Arg Cys Arg Met Ile Ala Gly Ala Asn Phe Tyr Ile Val Gly
            500                 505                 510
Arg Asp Pro Ala Gly Met Pro His Pro Glu Thr Lys Lys Asp Leu Tyr
        515                 520                 525
Glu Pro Thr His Gly Gly Lys Val Leu Ser Met Ala Pro Gly Leu Thr
    530                 535                 540
Ser Val Glu Ile Ile Pro Phe Arg Val Ala Ala Tyr Asn Lys Ile Lys
545                 550                 555                 560
Lys Ala Met Asp Phe Tyr Asp Pro Ala Arg His Glu Phe Asp Phe
                565                 570                 575
Ile Ser Gly Thr Arg Met Arg Lys Leu Ala Arg Glu Gly Glu Asp Pro
            580                 585                 590
Pro Asp Gly Phe Met Ala Pro Lys Ala Trp Lys Val Leu Thr Asp Tyr
        595                 600                 605
Tyr Arg Ser Glu Met Asp Lys Thr Asn
    610                 615

<210> SEQ ID NO 9
<211> LENGTH: 1845
<212> TYPE: DNA
<213> ORGANISM: Homo sapiens

<400> SEQUENCE: 9
atgtcgggga tcaagaagca aaagacggag aaccagcaga atccaccaa tgtagtctat       60 caggcccacc atgtgagcag gaataagaga gggcaagtgg ttggaacaag ggtgggttc      120 cgaggatgta ccgtgtggct aacaggtctc tctggtgctg aaaaacaac gataagtttt      180 gccctggagg agtaccttgt ctcccatgcc atcccttgtt actccctgga tggggacaat      240
gtccgtcatg gccttaacag aaatctcgga ttctctcctg gggacagaga ggaaaatatc      300
cgccggattg ctgaggtggc taagctgttt gctgatgctg gtctggtctg cattaccagc      360
tttatttctc cattcgcaaa ggatcgtgag aatgcccgca aaatacatga atcagcaggg      420
ctgccattct ttgaaatatt tgtagatgca cctctaaata tttgtgaaag cagagacgta      480
aaaggcctct ataaagggc cagagctggg gagattaaag gatttacagg tattgattct      540
gattatgaga aacctgaaac tcctgagcgt gtgcttaaaa ccaatttgtc cacagtgagt      600
gactgtgtcc accaggtagt ggaacttctg caagagcaga acattgtacc ctatactata      660
atcaaagata tccacgaact ctttgtgccg gaaaacaaac ttgaccacgt ccgagctgag      720
gctgaaactc tcccttcatt atcaattact aagctggatc tccagtgggt ccaggttttg      780
agcgaaggct gggccactcc cctcaaaggt tcatgcgggg agaaggagta cttacaggtt      840
atgcactttg acaccctgct agatgatggc gtgatcaaca tgagcatccc cattgtactg      900
cccgtctctg cagaggataa gacacggctg gaagggtgca gcaagtttgt cctggcacat      960
```

-continued

```
ggtggacgga gggtagctat cttacgagac gctgaattct atgaacacag aaaagaggaa    1020
cgctgttccc gtgtttgggg gacaacatgt acaaaacacc cccatatcaa atggtgatg    1080 gaaagtgggg actggctggt tggtggagac cttcaggtgc tggagaaaat aagatggaat    1140
gatgggctgg accaataccg tctgacacct ctggagctca acagaaatg taaagaaatg    1200 aatgctgatg cggtgtttgc attccagttg cgcaatcctg tccacaatgg ccatgccctg    1260
ttgatgcagg acacctgccg caggctccta gagagggct acaagcaccc ggtcctccta    1320
ctacaccctc tgggcggctg gaccaaggat gacgatgtgc tctagactg gcggatgaag    1380 cagcacgcgg ctgtgctcga ggaagggtc ctggatccca agtcaaccat tgttgccatc    1440
tttccgtctc ccatgttata tgctggcccc acagaggtcc agtggcactg caggtcccgg    1500
atgattgcgg gtgccaattt ctacattgtg ggagggacc ctgcaggaat gccccatcct    1560
gaaaccaaga aggatctgta tgaacccact catgggggca aggtcttgag catggccct    1620 ggcctcacct ctgtggaaat cattccattc cgagtggctg cctacaacaa agccaaaaaa    1680
gccatggact tctatgatcc agcaaggcac aatgagtttg acttcatctc aggaactcga    1740
atgaggaagc tcgcccggga aggagagaat cccccagatg gcttcatggc ccccaaagca    1800
tggaaggtcc tgacagatta ttacaggtcc ctggagaaga actaa                    1845
```

<210> SEQ ID NO 10
<211> LENGTH: 1851
<212> TYPE: DNA
<213> ORGANISM: Mus musculus

<400> SEQUENCE: 10

```
atgtctgcaa atttcaaaat gaaccataaa agagaccagc aaaaatccac caatgtggtc      60
taccaggccc atcatgtgag caggaacaag agaggacaag tggttggaac caggggagga    120
ttccgaggat gtaccgtgtg gctaacaggt ctctctggtg ctgggaaaac aaccataagc    180
tttgctttgg aagagtacct tgtatctcac gccatcccat gttactccct ggatgggac    240 aatgtccgtc atgccttaa taagaacctg gattctctg ccggggaccg agaagagaat    300
atccgccgga tcgcggaggt ggccaagctc tttgccgacg ccggcctggt ttgcatcacc    360
agctttatct ctccttttgc aaaggatcgt gagaatgccc gaaaaatcca cgaatcagca    420
ggactcccgt tctttgagat cttttgtagat gcgccttta aatatctgtga agccgagac    480 gtaaaaggac tctacaaacg agcccgagca ggagagatta aagggttac aggcatcgat    540 tctgactatg agaaacctga actccagag tgtgtgctga agaccaactt gtcttcagta    600
agcgactgtg tgcaacaggt ggtggaactt ttgcaggagc agaacattgt accccacacc    660
accatcaaag gcatccacga actctttgtg ccagaaaaca aagtcgatca aatccgagct    720
gaggcagaga ctctcccatc actaccaatt accaagctgg atctgcagtg ggtgcagatt    780
ctgagtgaag gctgggccac tcccctcaaa ggctttatgc gggagaagga atacttgcaa    840
actctacact tcgacactct actggacgat ggagtcatca acatgagtat tcccattgta    900
ttgcccgttt ctgcggatga caaggcacgg ctcgaagggt gcagcaaatt tgccttgatg    960
tacgaaggtc ggagggtcgc tctattacag gaccctgaat tctatgagca taggaaagag    1020
gagcgttgtt ctcgtgtgtg gggaacagcc actgcaaagc accccccatat caaaatggtg    1080 atggaaagtg gggactggct tgttggtgga gacctacagg tgctagagag aataaggtgg    1140
gacgatgggc tggaccaata ccgccttacg cctctggaac tcaaacagaa gtgtaaagac    1200
```

```
atgaatgctg atgccgtgtt tgcattccag ttgcgcaatc ctgtccacaa tggtcatgcc      1260
ctcctgatgc aggacacccg ccgcaggctc ctggagaggg gttacaagca cccagtcctc      1320
ctgctccacc ctcttggggg ctggaccaag gacgatgacg tacctctgga atggaggatg      1380
aaacagcatg cagctgtact ggaggaaagg gtcctggatc ccaagtcaac tattgttgcc      1440
atctttccat ctcctatgtt atacgctggt cccacagagg tccagtggca ttgcagatgc      1500
cggatgattg caggagccaa tttctacatt gtgggtaggg atcccgcagg aatgccccat      1560
cctgagacaa agaaagacct atatgaaccc acccacgggg gcaaggtctt gagtatggcc      1620
cctggcctta cctctgtgga ataattccg ttccgagtgg ctgcctacaa taaaattaaa      1680
aaggccatgg acttttatga tccagcaagg cacgaggagt ttgacttcat ctcaggaact      1740
cgcatgagga agctcgcccg ggaaggagaa gatcccccag atggcttcat ggccccgaaa      1800
gcgtggaaag tgttgacaga ttactacagg tctctggaga agaccaacta g             1851
```

```
<210> SEQ ID NO 11
<211> LENGTH: 21
<212> TYPE: DNA
<213> ORGANISM: Homo sapiens

<400> SEQUENCE: 11
gccagccagc atgtcgggga t                                                21

<210> SEQ ID NO 12
<211> LENGTH: 24
<212> TYPE: DNA
<213> ORGANISM: Homo sapiens

<400> SEQUENCE: 12
acctgaaact cctgagcgtg tgct                                             24

<210> SEQ ID NO 13
<211> LENGTH: 21
<212> TYPE: DNA
<213> ORGANISM: Homo sapiens

<400> SEQUENCE: 13
gatgtgcctc tagactggcg g                                                21

<210> SEQ ID NO 14
<211> LENGTH: 24
<212> TYPE: DNA
<213> ORGANISM: Homo sapiens

<400> SEQUENCE: 14
gagcacttca gaaagaaact ctgg                                             24

<210> SEQ ID NO 15
<211> LENGTH: 21
<212> TYPE: DNA
<213> ORGANISM: Homo sapiens

<400> SEQUENCE: 15
catccgccag tctagaggca c                                                21

<210> SEQ ID NO 16
<211> LENGTH: 21
<212> TYPE: DNA
<213> ORGANISM: Homo sapiens

<400> SEQUENCE: 16
```

```
aggtgtcaga cggtattggt c                                          21

<210> SEQ ID NO 17
<211> LENGTH: 23
<212> TYPE: DNA
<213> ORGANISM: Homo sapiens

<400> SEQUENCE: 17
gtcactcact gtggacaaat tgg                                        23

<210> SEQ ID NO 18
<211> LENGTH: 21
<212> TYPE: DNA
<213> ORGANISM: Homo sapiens

<400> SEQUENCE: 18
cacctcagca atccggcgga t                                          21

<210> SEQ ID NO 19
<211> LENGTH: 20
<212> TYPE: DNA
<213> ORGANISM: Mus musculus

<400> SEQUENCE: 19
tctggcacaa agagttcgtg                                            20

<210> SEQ ID NO 20
<211> LENGTH: 22
<212> TYPE: DNA
<213> ORGANISM: Mus musculus

<400> SEQUENCE: 20
gccagtttgt aaccgagtat tc                                         22

<210> SEQ ID NO 21
<211> LENGTH: 22
<212> TYPE: DNA
<213> ORGANISM: Mus musculus

<400> SEQUENCE: 21
gcaattggat acagagcagc ta                                         22

<210> SEQ ID NO 22
<211> LENGTH: 22
<212> TYPE: DNA
<213> ORGANISM: Mus musculus

<400> SEQUENCE: 22
gacaatgtcc gtcatggcct ta                                         22

<210> SEQ ID NO 23
<211> LENGTH: 21
<212> TYPE: DNA
<213> ORGANISM: Mus musculus

<400> SEQUENCE: 23
attcccattg tattgcccgt t                                          21

<210> SEQ ID NO 24
<211> LENGTH: 21
<212> TYPE: DNA
<213> ORGANISM: Mus musculus
```

```
<400> SEQUENCE: 24
aacgggcaat acaatgggaa t                                              21

<210> SEQ ID NO 25
<211> LENGTH: 22
<212> TYPE: DNA
<213> ORGANISM: Mus musculus

<400> SEQUENCE: 25
gataaagctg gtgatgcaaa cc                                             22

<210> SEQ ID NO 26
<211> LENGTH: 20
<212> TYPE: DNA
<213> ORGANISM: Mus musculus

<400> SEQUENCE: 26
catgggatgg cgtgagatac                                                20

<210> SEQ ID NO 27
<211> LENGTH: 23
<212> TYPE: DNA
<213> ORGANISM: Mus musculus

<400> SEQUENCE: 27
cataagcttt gctttggaag agt                                            23

<210> SEQ ID NO 28
<211> LENGTH: 21
<212> TYPE: DNA
<213> ORGANISM: Homo sapiens

<400> SEQUENCE: 28
gcatgtccag acagacacca c                                              21

<210> SEQ ID NO 29
<211> LENGTH: 333
<212> TYPE: DNA
<213> ORGANISM: Homo sapiens
<220> FEATURE:
<221> NAME/KEY: misc_feature
<222> LOCATION: (1)...(333)
<223> OTHER INFORMATION: D19Mit13 locus and flanking sequences
<223> OTHER INFORMATION: n = A,T,C or G; at nucleotide positions 23 and
      305

<400> SEQUENCE: 29
ctgactatga gaaacctgaa acnccagagt gtgtgctgaa gaccaacctg tcttcagtaa     60
gcgactgtgt gcaacaggtg gtggaacttt tgcaggagca ggtaggaggg tggttcttgc    120
cagtgtgttc agtgtgtgtg tgtgtgtgtg tgtgtgtgtg tgcgtgtgca tgtgtgtgtg    180
catgtgtgtg tgcgtgtgca tgtgtgtgtg ttgaaagata atctgagttt ctttattccc    240
tggccaatct cagtaactat tgccaatttc gtttcccaca gaacattgta ccccacacca    300
ccatnaaagg catccacgaa ctctttgtgc cag                                 333

<210> SEQ ID NO 30
<211> LENGTH: 18
<212> TYPE: DNA
<213> ORGANISM: Homo sapiens
<220> FEATURE:
<223> OTHER INFORMATION: Nucleotide positions +1414 through +1431 of
      PAPSS2 coding sequence
```

-continued

```
<400> SEQUENCE: 30
gatcccaagt caaccatt                                                    18

<210> SEQ ID NO 31
<211> LENGTH: 6
<212> TYPE: PRT
<213> ORGANISM: Homo sapiens
<220> FEATURE:
<223> OTHER INFORMATION: Partial PAPSS2 peptide sequence; amino acid
      residues 472 through 477

<400> SEQUENCE: 31

Asp Pro Lys Ser Thr Ile
 1               5

<210> SEQ ID NO 32
<211> LENGTH: 18
<212> TYPE: DNA
<213> ORGANISM: Homo sapiens
<220> FEATURE:
<221> NAME/KEY: mutation
<222> LOCATION: (0)...(0)
<223> OTHER INFORMATION: Nucleotide positions +1414 through +1431 of
      PAPSS2 coding sequence with mutation c to a at nucleotide
      position +1424

<400> SEQUENCE: 32
gatcccaagt aaaccatt                                                    18

<210> SEQ ID NO 33
<211> LENGTH: 3
<212> TYPE: PRT
<213> ORGANISM: Homo sapiens
<220> FEATURE:
<223> OTHER INFORMATION: Partial  truncated PAPSS2 peptide sequence;
      amino acid residues 472-474 plus stop at position 475

<400> SEQUENCE: 33

Asp Pro Lys
 1
```

3-PHOSPHOADENOSINE-5-PHOSPHOSULFATE (PAPS) SYNTHETASE PROTEINS AND METHODS FOR TREATING OSTEOARTHRITIC DISORDERS

This application is a division of U.S. Ser. No. 09/399,212 filed Sep. 17, 1999, now abandoned, and is further related to U.S. Ser. No. 09/898,200, filed Jul. 2, 2001, which is a division of U.S. Ser. No. 09/399,212.

The U.S. Government has a paid-up license in this invention and the right in limited circumstances to require the patent owner to license others on reasonable terms as provided for by the terms of grants HD22657 and AR02038 awarded by the NIH.

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. The Field of the Invention

This invention relates to the medical arts. In particular, it relates to a genetic marker that is useful for diagnosing or treating spondyloepimetaphyseal dysplasia and for identifying genetic carriers of heritable alleles associated with spondyloepimetaphyseal dysplasia.

2. Discussion of the Related Art

Osteochondrodysplasias are a genetically heterogeneous group of disorders related to cartilage producing cells. Abnormalities in cartilage formation can cause defects in bone deposition, skeletal development, linear growth, and the continued maintenance of cartilage and bone. (Reviewed in Mundlos, S. and Olsen, B. R., *Heritable diseases of the skeleton. Part II: Molecular insights into skeletal development-matrix components and their homeostasis*, FASEB J. 11(4):227–33 [1997]).

There are numerous and disparate causes of osteochondrodysplasias. (Horton, W. A., *Molecular genetic basis of the human chondrodysplasias*, Endocrinol. Metab. Clin. North Am. 25(3):683–97 [1996]). A significant number are due to defects in the collagen genes themselves. (Reviewed in Williams, C. J. and Jiminez, S. A., *Heritable diseases of cartilage caused by mutations in collagen genes*, J. Rheumatol. Suppl. 43:28–33 [1995]; Byers, P. H., *Molecular genetics of chondrodysplasias, including clues to development, structure, and function*, Curr. Opin. Rheumatol. 6(3):345–50 [1994]). In addition to collagen defects, several forms of osteochondrodysplasias are caused by mutations in the cartilage oligomeric matrix protein (COMP). (Ikegawa, S., et al., *Novel and recurrent COMP mutations in preudoachondroplasia and epiphyseal dysplasia*, Hum. Genet. 103(6):633–8 [1998]; Briggs, M. D., et al., *Diverse mutations in the gene for cartilage oligomeric matrix protein in the pseudoachondroplasia-multiple epiphyseal dysplasia disease spectrum*, Am. J. Hum. Genet. 62(2):311–9 [1998]; Briggs, M. D., et al., *Pseudoachondroplasia and multiple epiphyseal dysplasia due to mutations in the cartilage matrix protein gene*, Nat. Genet. 10(3):330–6 [1995]; Ballo, R., et al., *Multiple epiphyseal dysplasia, ribbing type: a novel point mutation in the COMP gene in a South African family*, Am. J. Med. Genet. 68(4):396–400 [1997]).

Still other osteochondrodysplasias have been found to be caused by defects in secreted peptide growth factors and their receptors. (E.g., Thomas, J. T., et al., *A human chondroplysplasia due to a mutation in a TGF-β superfamily member*, Nat. Genet. 12(3):315–7 [1996]; Bonaventure, J., et al., *Common mutations in the gene encoding FGFR-3 account for achondroplasia, hypochondroplasia and thanatophoric dysplasia*, Acta Paediatr. Suppl. 417:33–38 [1996]).

Finally, mutations in genes which affect protein sulfation cause some forms of osteochondrodysplasia. Protein sulfation is a post-translational modification carried out by all cells. (Lipmann, F., *Biological sulfate activation and transfer*, Science 128:575–580 [1958]). The primary source of sulfur for the sulfation pathway is free sulfate, which can be transported into the cytoplasm by one of a variety of transmembrane symporter or antiporter molecules. (Elgavish, A., et al., *Sulfate transport in human lung fibroblasts (IMR-90)*, J. Cell Physiol. 125:243–250 [1985]; Markovich, D., et al., *Expression cloning of rat renal $Na+/SO_4^{(2-)}$ cotransport*, Proc. Natl. Acad. Sci. U.S.A. 90:8073–8077 [1993]; Bissig, M., et al., *Functional expression cloning of the canalicular sulfate transport system of rat hepatocytes*, J. Biol.Chem. 269:3017–3021 [1994]; Hastbacka, J., et al., *The diastrophic dysplasia gene encodes a novel sulfate transporter: positional cloning by fine-structure linkage disequilibrium mapping*, Cell 78:1073–1087 [1994]; Everett, L. A., et al., *Pendred syndrome is caused by mutations in a putative sulphate transporter gene (PDS)*, Nat. Genet. 17:411–422 [1997]).

Within the cytoplasm, sulfate is activated to a high energy form in two enzymatic steps (Geller, D. H., et al., *Co-purification and characterization of ATP-sulfurylase and adenosine-5'-phosphosulfate kinase from rat chondrosarcoma*, J. Biol. Chem. 262:7374–7382 [1987]). First, utilizing ATP and sulfate as substrates, an ATP sulfurylase activity catalyzes the synthesis of adenosine 5'-phosphosulfate (APS). Subsequently, an APS kinase activity catalyzes the phosphorylation of the APS to generate 3'-phosphoadenosine 5'-phosphosulfate (PAPS). PAPS is the universal bioactivated sulfate donor used in all known post-translational sulfation reactions.

Secreted extracellular matrix proteins are post-translationally sulfated in the Golgi, and delivery of PAPS to the Golgi is mediated by a PAPS translocase activity. Microsomal proteins with PAPS binding activity have been identified (Mandon, E. C., et al., *Purification of the golgi adenosine 3'-phosphate 5'-phosphosulfate transporter, homodimer within the membrane*, Proc. Natl. Acad. Sci. U.S.A. 91:10707–10711 [1994]; Ozeran, J. D., et al., *Kinetics of PAPS translocase: evidence for an antiport mechanism*, Biochemistry 35:3685–3694 [1996]), but the tissue specificity and the contribution of these proteins to PAPS transport remains unknown. Following transport, sulfation reactions are carried out by substrate-specific sulfotransferases. A major class of sulfation substrates within the Golgi is the side-chains of proteoglycans, which are abundant structural proteins of the extracellular matrices of many tissues. Proteoglycans are particularly abundant in the extracellular matrix of cartilage.

Direct evidence that sulfation of extracellular matrix proteins is essential for proper matrix function was revealed by the identification of mutations in the diastrophic dysplasia sulfate transporter, DTDST. (Hastbacka et al. [1994]). Mutations in the DTDST gene produce a spectrum of recessively inherited osteochondrodysplasia phenotypes. (Hastbacka et al. [1994]; Hastbacka, J., et al., *Atelosteogenesis type II is caused by mutations in the diastrophic dyplasia sulfate transporter gene (DTDST): Evidence for a phenotypic series involving three chondrodysplasias*, Am. J.

Hum. Genet. 58:255–262 [1996]; Superti-Furga, et al., *A family of chondrodysplasias caused by mutations in the diastrophic dysplasia transporter gene and associated with impaired sulfation of proteoglycans*, Ann. N.Y. Acad. Sci. 785:195–201 [1996]). The severity of the three known disorders, i.e., the moderately severe diastrophic dysplasia phenotype and the lethal forms, atelosteogenesis type II and achondrogenesis type IB, is correlated with the consequences of the mutations on the activity of the transporter. (Superti-Furga, A, et al. *Achondrogenesis type IB is caused by mutations in the diastrophic dysplasia sulfate transporter gene*, Nature Genet. 12:100–02 (1996). The mutations lead to dramatically reduced proteoglycan sulfation in cartilage, particularly the chondroitin sulfate side chains of aggrecan. However, even in the most severe disorder in the group, some proteoglycan sulfation can be measured. (Rossi A., et al., *Undersulfation of proteoglycans synthesized by chondrocytes from patient with achondrogenesis type 1B homozygous for an L483P substitution in the diastrophic dysplasia sulfate transporter*, J. Biol. Chem. 271:18456–64 [1996]; Rossi, A., et al., *Undersulfation of cartilage proteoglycans ex vivo and increased contribution of amino acid sulfur to sulfation in vitro in McAlister dysplasia/atelosteogenesis type 2*, Eur. J. Biochem. 248:741–47 [1997]; Rossi, A., et al., *Proteoglycan sulfation in cartilage and cell cultures from patients with sulfate transporter chondrodyplasias: relationship to clinical severity and indications on the role of cellular sulfate production, Matrix Biology* 17:361–69[1998]).

Biochemical evidence that a defect in another step in the sulfation pathway can produce an osteochondrodysplasia phenotype was provided by studies in the brachymorphic (bm) mouse. The brachymorphic phenotype is characterized by disproportionate short-limb dwarfism, a short spine and tail, and a domed skull. (Lane & Dickie [1968]). The brachymorphic mouse also exhibits an increased bleeding time, but tests of platelet function, including aggregation and secretion, have so far failed to reveal specific functional deficits in brachymorphic platelets. (Rusiniak, M. E., et al., *Molecular markers near the mouse brachymorphic (bm) gene, which affects connective tissues and bleeding time*, Mamm. Genome 7:98–102[1996]).

In brachymorphic mice, abnormal growth plates with a structurally abnormal cartilage extracellular matrix and short chondrocyte columns, with comparatively unaligned cells, are apparent on histologic analysis. (Lane & Dickie [1968]; Orkin et al. [1976]; Orkin et al. [1977]; Miller, W. A. & Flynn-Miller, K. L., *Achondroplastic, brachymorphic and stubby chondrodystophies in mice*, J. Comp. Pathol. 86:349–63 [1976]). Cartilage from this recessively inherited mutant phenotype shows small, diffuse proteoglycan granules and reduced staining for sulfated glycosaminoglycans, consistent with a defect affecting sulfation of the proteoglycans of the cartilage extracellular matrix. (Lane, P. & Dickie, M. M., *Three recessive mutations producing diproportionate dwarfing in mice: achondroplasia, brachymorphic, and stubby*, J. Hered. 59:300–08 [1968]). In brachymorphic mice, proteoglycan granules show a 50% reduction in size in the reserve zone of the growth plate matrix, and are difficult to identify in the proliferative and hypertrophic zones. (Orkin, R. W., et al., *Undersulfated chondroitin sulfate in the cartilage matrix of brachymorphic mice*, Dev. Biol. 50:82–94 [1976]; Orkin, R. W., et al., *Defects in the cartilaginous growth plates of brachymorphic mice*, J. Cell Biol. 73:287–99 [1977]). This suggests that reduced proteoglycan sulfation affects the signals that regulate growth plate chondrocyte maturation. Heparan sulfate proteoglycans have been implicated in the sequestration and presentation of growth factors, particularly fibroblast growth factors, to receptors at the cell surface. (Rapraeger, A. C., et al., *Requirement of heparan sulfate for bFGF-mediated fibroblast growth and myoblast differentiation*, Science 252:1705–08 [1991]; Yayon, A., et al., *Cell surface, heparin-like molecules are required for binding of basic Fibroblast Growth Factor to its high-affinity receptor*, Cell 64:841–48 [1991]; Schlessinger, J., et al., *Regulation of growth factor activation by proteoglycans: What is the role of the low affinity receptors?*, Cell 83:357–60 [1995]). Skeletal defects in mice lacking heparan sulfate 2-sulfotransferase include dwarfism, with shortened long bones, ribs and spine, implying a specific role for heparan sulfate proteoglycans in skeletal development. (Bullock, S. I., et al., *Renal agenesis in mice homozygous for a gene trap mutation in the gene encoding heparan sulfate 2-sulfotransferase*, Genes Dev. 12:1894–1906 [1998]).

Indeed, reduced activities of both ATP sulfurylase and APS kinase, and decreased synthesis of chondroitin sulfate, have been demonstrated in bm mice. (Schwartz, N. B., et al., *Defective PAPS-synthesis in epiphyseal cartilage from brachymorphic mice*, Biochem. Biophys. Res. Commun. 82:173–78 [1978]; Sugahara, K. & Schwartz, N. B., *Defect in 3'-phosphoadenosine 5'-phosphosulfate formation in brachymorphic mice. Proc. Natl. Acad. Sci. U.S.A.* 76:6615–18 [1979]). The ATP sulfurylase and APS kinase activities in brachymorphic mouse tissues co-purified. (Geller, D. H., et al. [1987]; Lyle, S., et al., *Rat chondrosarcoma ATP sulfurylase and adenosine 5'-phosphosulate kinase reside on a single bifunctional protein*, Biochemistry 33:5920–25 [1994]). The functional activity of the APS kinase was reduced to a greater extent than was that of the ATP sulfurylase, suggesting that brachymorphism resulted from a structural mutation that affected channeling APS from the carboxyl-terminal sulfurylase activity to the amino-terminal kinase. (Lyle, S., et al., *Sulfate-activating enzymes in normal and brachymorphic mice: evidence for a channeling defect*, Biochemistry 34:940–45 [1995]).

A cDNA encoding a murine bifunctional ATP-sulfurylase/APS-kinase enzyme (known as Papss1, formerly known as Atpsk1) was isolated from brachymorphic mice and studied by mutational analysis. (Li, H. et al., *The isolation and characterization of cDNA encoding the mouse bi-functional ATP sulfurylase-adenosine 5'-phosphosulfate kinase*, J. Biol. Chem. 270(49):29453–59 [1995]; Deyrup, A. T. et al., *Deletion and site-directed mutagenesis of the ATP-binding motif (P-loop) in the bifunctional murine ATP-sulfurylase/adenosine 5'-phosphosulfate kinase enzyme*, J. Biol. Chem. 273(16):9450–56 [1998]). Subsequently, bifunctional enzyes having ATP-sulfurylase (E.C. 2.7.7.4)/APS-kinase (E.C. 2.7.1.25) activities were designated "PAPS synthetase" (PAPSS; also known as ASAPK and ATPSK).

The bm mutation was placed on the mouse phenotypic map by Lane and Dickie (1968). Subsequent application of microsatellite markers to mice from a large backcross localized the bm mutation to a 2.5 cM region located at approximately 32 cM on mouse chromosome 19. (O'Brien, E. P., et al., *Molecular map of chromosome 19 including three genes affecting bleeding time: ep, ru and bm*, Mamm. Genome 5:356–60 [1994; Rusiniak, M. E., et al. (1996]). In addition, a liver cancer susceptibility gene, Hcs6, has been localized near bm in mouse strain C3H/He. (Manenti, G., et al. [1994]).

The bm mutation co-localized with a PAPSS gene. (Kurima, K. et al., *A member of a family of sulfate-activating enzymes causes murine brachymorphism*, Proc. Natl. Acad.

Sci. 95(15):8681–85 [1998]; Sugahara, K. and Schwartz, N. B., *Defect in 3'-phosphoadenosine 5'-phosphosulfate formation in brachymorphic mice*, Proc. Nat. Acad. Sci. 76(12):6615–18 [1979]). Although brachymorphic mouse liver shows decreased PAPSS activity, the brachymorphic phenotype does not manifest any grossly recognizable liver defects. It has been observed that brachymorphic mouse liver has a decreased ability to esterify xenobiotic carcinogens with sulfate (Lyman, S. D. & Poland, A., *Effect of the brachymorphic trait in mice on xenobiotic sulfate ester formation*, Biochem. Pharmacol. 32:3345–50 [1983]), which implies that altered susceptibility to such agents could result from defects in a PAPSS gene. Consistent with this hypothesis, brachymorphic mice have decreased susceptibility to carcinogen-induced hepatocarcinoma, presumably due to a decreased ability to generate sulfated carcinogens. (Boberg, E. W., et al., *Strong evidence from studies with brachymorphic mice and pentachlorophenol that 1'-sulfooxysafrole is the major ultimate electrophilic and carcinogenic metabolite of 1'-hydroxysafrole in mouse liver*, Cancer Res. 43:5163–73 [1983]; Lai, C. C., et al., *Initiation of hepatocarcinogenesis in infant male B6C3F1 mice by N-hydroxy-2-aminofluorene depends primarily on metabolism to N-sulfooxy-2-aminofluorene and formation of DNA-(deoxyguanosin-8-yl)-2-aminofluorene adducts*, Carcinogenesis 8:471–78 [1987]).

PAPSS enzymes have been isolated and characterized in non-murine systems, for example, in association with rat chondrosarcomas. (Rosenthal, E. and Leustek, T., *A multifunctional Urechis caupo protein, PAPS synthetase, has both ATP sulfurylase and APS kinase activities*, Gene 165(2):243–48 [1995]; Schwartz, N. B., et al., *Sulfate activation and transport in mammals; system components and mechanisms*, Chem. Biol Interact. 109(1–3):143–51 [1998]; Lyle, S. et al., *Rat chondrosarcoma ATP sulfurylase and adenosine 5'-phosphosulfate kinase reside on a single bifunctional protein*, Biochemistry 33(19):5920–25 [1994]; Lyle, S. et al., *Intermediate channeling between ATP sulfurylase and adenosine 5'-phosphosulfate kinase from rat chondrosarcoma*, Biochemistry 33(22):6822–27 [1994]). Human cDNAs for PAPSS have also been cloned, and their activities have been analyzed biochemically and mutationally. (Yanagisawa, K. et al., *cDNA cloning, expression, and characterization of the human bifunctional ATP sulfurylase/adenosine 5'-phosphosulfate kinase enzyme*, Biosci. Biotechnol. Biochem. 62(5):1037–40 [1998]; Girard, J. P., et al., *Sulfation in high endothelial venules: cloning and expression of the human PAPS synthetase*, FASEB J. 12(7):603–12 [1998]; Venkatachalam, K. V. et al., *Molecular cloning, expression, and characterization of human bifunctional 3'-phosphoadenosine 5'-phosphosulfate synthase and its functional domains*, J. Biol. Chem. 273(30):19311–20 [1998]; Ventkatachalam, K. V., et al., *Site-selected mutagenesis of a conserved nucleotide binding HXGH motif located in the ATP sulfurylase domain of human bifunctional 3'-phosphoadenosine 5'-phosphosulfate synthase*, J. Biol. Chem. 274(5):2601–04 [1999]).

Phenotypically analogous to murine brachymorphism, is spondyloepimetaphyseal dysplasia (SEMD) in humans. SEMD is a subgroup of osteochondrodysplasias affecting skeletal development, linear bone and cartilage growth, and bone and cartilage maintenance. Effects of SEMD can include dwarfism, stunted or malformed limbs, enlarged joints, kyphoscoliosis (spinal warping), and brachydactyly (short fingers and toes). SEMD typically runs in families, and can be inherited in autosomal dominant or recessive manners. (Ahmad, M. et al., *Distinct, autosomal recessive form of spondyloepimetaphyseal dysplasia segregating in an inbred Pakistani kindred*, Am. J. Med. Genet. 78(5):468–73 [1998]; Figuera, L. E., et al., *Spondyloepimetaphyseal dysplasia (SEMD) Shohat type*, Am. J. Med. Genet. 51(3):213–15 [1994]; Shohat, M. et al., *New form of spondyloepimetaphyseal dysplasia (SEMD) in Jewish family of Iraqi origin*, Am. J. Med. Genet. 46(4):358–62, [1993]; Whyte, M. P. et al., *Hypotrichosis with spondyloepimetaphyseal dysplasia in three generations; a new autosomal dominant syndrome*, Am. J. Med. Genet. 36(3):288–91 [1990]; Gertner, J. M., et al., *Linkage studies of a Missouri kindred with autosomal dominant spondyloepimetaphyseal dysplasia (SEMD) indicate genetic heterogeneity*, J. Bone Miner. Res. 12(8):1204–9, [1997]).

A nonsense mutation in a novel, cartilage-specific human PAPSS (PAPSS2, formerly ATPSK2), has been indicated as the cause of a recessive form of SEMD in an inbred Pakistani family. (Ahmad, M., et al., *A distinct, autosomal recessive form of spondyloepimetaphyseal dysplasia segregating in an inbred Pakistani kindred*, Am. J. Med. Genet. 78:468–73 [1998]; ul Haque, M. F., et al., *Mutations in orthologous genes in human spondyloepimetaphyseal dysplasia and the brachymorphic mouse*, Nat. Genet. 20(2):157–62 [1998]). Genome-wide linkage studies localized the disease gene for this dwarfing condition to chromosome 10q23–24, in a region syntenic with the locus for the bm locus on mouse chromosome 19. (ul Haque, M. F., et al. [1998]). This disorder, designated SEMD Pakistani type, is characterized by short, bowed lower limbs, enlarged knee joints, kyphoscoliosis, a mild generalized brachydactyly, and early-onset degenerative joint disease in the hands and knees. Radiographs of patients with SEMD Pakistani type show delayed epiphyseal ossification, especially at the hips and knees, and platyspondyly.

Currently, there are only a few methods of detecting bone related diseases. (Eg., Klock, J. C., *Chondroitin sulfate as a marker for bone resorption*, U.S. Pat. No. 5,869,273; Takeshita, S. et al., *Bone-related sulfatase-like protein and process for its production*, U.S. Pat. No. 5,627,050). DNA-based diagnostic approaches have been suggested for some type 2 collagen disorders, such as Stickler syndrome, spondyloepiphyseal dysplasia, and achondrogenesis; achondroplasia (a defect in the fibroblast growth factor receptor 3 (FGFR3) gene); the collagen oligomeric matrix protein (COMP) disorders pseudoachondroplasia and multiple epiphyseal dysplasia, and others. (E.g., Ritvaniemi, *Arthritis and Rheumatism* 38:999–1004 [1995]; Shiang et al., *Mutations in the transmembrane domain of FGFR3 cause the most common genetic form of dwarfism, achondroplasia*, Cell 78:335–42 [1994]; Briggs et al., *Pseudoachondroplasia and multiple epiphyseal dysplasia due to mutations in the cartilage of oligomeric matrix protein gene*, Nature Genetics 10:330–36 [1995]; Superti-Ferga et al., *Recessively inherited multiple epiphyseal dysplasia with normal stature, club foot, and double layered patella caused by DTDST mutation*, J. Med. Genet. 36:621–24 [1999]). But most reported diagnostic methods relate to osteogenic proteins. (E.g., Khandke, K. M., et al., *Chromatographic process for the copurification of chondroitinase I and II proteins from Proteus vulgaris*, U.S. Pat. No. 5,525,500; Parsons, T. F., et al., *Osteogenic Factors*, U.S. Pat. No. 5,106,626; Oppermann, H., et al., *Cartilage and bone-inducing proteins*, U.S. Pat. No. 5,750,651).

Accordingly, a reliable method is still needed for diagnosing SEMD, detecting the presence of SEMD in recessive carriers, and for treating osteoarthritic disorders, including osteochondrodysplasias, that are caused or aggravated by deficient PAPS synthetase activity. The present invention provides these and other advantages, as described herein.

SUMMARY OF THE INVENTION

The present invention relates to an isolated polynucleotide or to a nucleic acid construct that comprises a nucleic acid segment encoding a 3'-phosphoadenosine-5'-phosphosulfate (PAPS) synthetase (PAPSS), particularly, a human PAPSS2 nucleotide sequence of (SEQ. ID. NO.:1) or an orthologous murine Papss2 nucleotide sequence (SEQ. ID. NO.:2), sequences complementary to either one of them, degenerate coding sequences, or gene-specific fragments of (SEQ. ID. NOS.:1 and 2). The present polynucleotides and nucleic acid constructs containing PAPSS2 and Papss2 nucleotide sequences include RNA; DNA; and chimeric RNA/DNA. Embodiments include probes, primers, and expression vectors containing PAPSS2- and Papss2-specific nucleotide sequences.

The present invention also relates to a genetically modified vertebrate cell containing a nucleic acid construct of the present invention and to a non-human vertebrate containing the cell. The present invention also relates to human PAPSS2 and murine Papss2 proteins encoded by the present polynucleotide or nucleic acid construct, including fusion proteins that contain, together with a PAPSS2 or Papss2 amino acid sequence, any other predetermined polypeptide sequence. The present invention also relates to antibodies and antibody fragments that selectively bind the PAPSS2 or Papss2 protein.

The present invention is also directed to a method of diagnosing spondyloepimetaphyseal dysplasia (SEMD) in a human subject. The method involves amplifying nucleic acids from a sample that define an PAPSS2 gene sequence, or a gene-specific fragment thereof; and analyzing the amplified nucleic acids for the presence of homozygosity for a variant allele of PAPSS2. The sample is a bodily substance containing human nucleic acid, for example a blood sample, obtained from a human subject having at least one symptom of SEMD. Homozygosity for a variant allele of PAPSS2 is diagnostic for SEMD in the human subject. In particular, the present invention also relates to a method of diagnosing SEMD Pakistani-type in a human subject. But the present invention also relates to a method of identifying a heterozygous human carrier of an SEMD-associated allele.

The present invention provides a genetic testing kit for diagnosing SEMD or for identifying a human carrier of SEMD, including SEMD Pakistani-type. The genetic testing kit contains oligonucleotide primers of the present invention.

Also, nucleic acid constructs of the present invention are used in a method of gene therapy for treating a human subject having an osteoarthritic disorder that is caused or aggravated by deficient enzymatic sulfation activity. The present invention is also related to a protein therapy method for treating a human subject having an osteoarthritic disorder that is caused or aggravated by deficient enzymatic sulfation activity. This method employs the inventive PAPSS2 fusion protein.

DETAILED DESCRIPTION OF THE PREFERRED EMBODIMENTS

Figure 1:
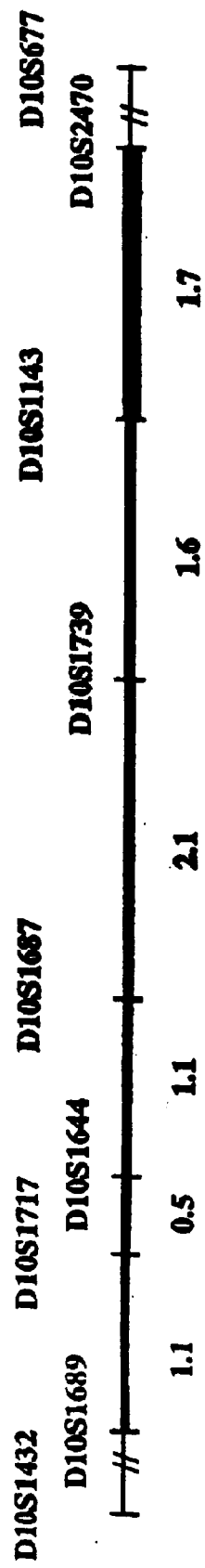
FIG. 1 shows a genetic map of the interval containing the SEMD disease gene on human chromosome 10. Distances between loci are given in centimorgans (cM).

The present invention relates to an isolated polynucleotide, of natural origin or a nucleic acid construct, that comprises a nucleic acid segment encoding an ATP sulfurylase/APS kinase, i.e., a PAPS synthetase (PAPSS), particularly, a human PAPSS2 nucleotide sequence of (SEQ. ID. NO.:1) or an orthologous murine Papss2 nucleotide sequence (SEQ. ID. NO.:2).

The human PAPSS2 gene is located on chromosome 10 at locus 10q23–24. (ul Haque, M. F., et al. [1998]). More specifically, the PAPSS2 gene region is flanked by microsatellite markers D10S1143 and D10S2470. (See FIG. 1; C. Dib et al., *A comprehensive genetic map of the human genome based on 5,264 microsatellites*, Nature 380(6570): 152–54 [1996]). The cloned human PAPSS2 nucleotide sequence is the following (GenBank accession AF091242; transcriptional start site [underlined] commences at position +1):

-80 CTGCTGCCGC CGCCGCCGCC GCCGTCCCTG CGTCCTTCGG TCTCTGCTCC CGGGACCCGG
-20 CTCCGCCGCA GCCAGCCAGC <u>ATG</u>TCGGGGA TCAAGAAGCA AAAGACGGAG AACCAGCAGA
+41 AATCCACCAA TGTAGTCTAT CAGGCCCACC ATGTGAGCAG GAATAAGAGA GGGCAAGTGG
+101 TTGGAACAAG GGTGGGITC CGAGGATGTA CCGTGTGGCT AACAGGTCTC TCTGGTGCTG
+161 GAAAAACAAC GATAAGTT=T GCCCTGGAGG AGTACCTTGT CTCCCATGCC ATCCCTTGTT
+221 ACTCCCTGGA TGGGGACAAT GTCCGTCATG GCCTTAACAG AAATCTCGGA TTCTCTCCTG
+281 GGGACAGAGA GGAAAATATC CGCCGGATTG CTGAGGTGGC TAAGCTGTTR GCTGATGCTG
+341 GTCTGGTCTG CATTACCAGC TTrATTTCTC CATTCGCAAA GGATCGTGAG AATGCCCGCA
+401 AAATACATGA ATCAGCAGGG CTGCCATTCT TTGAAATATT TGTAGATGCA CCTCTAAATA
+461 TTTGTGAAAG CAGAGACGTA AAAGGCCTCT ATAAAAGGGC CAGAGCTGGG GAGATTAAAG
+521 GATTACAGG TATTGATTCT GATTATGAGA AAC- CTGAAAC TCCTGAGCGT GTGCTTAAAA

+581 CCAATTRGTC CACAGTGAGT GACTGTGTCC ACCAGGTAGT GGAACTTCTG CAAGAGCAGA
+641 ACATTGTACC CTATACTATA ATCAAAGATA TCCACGAACT CTTTGTGCCG GAAAACAAAC
+701 TTGACCACGT CCGAGCTGAG GCTGAAACTC TCCCTTCATT ATCAATTACT AAGCTGGATC
+761 TCCAGTGGGT CCAGGTTTTG AGCGAAGGCT GGGCCACTCC CCTCAAAGGT TTCATGCGGG
+821 AGAAGGAGTA CTTACAGGTT ATGCACTTTG ACACCCTGCT AGATGATGGC GTGATCAACA
+881 TGAGCATCCC CATTGTACTG CCCGTCTCTG CAGAGGATAA GACACGGCTG GAAGGGTGCA
+941 GCAAGTTTGT CCTGGCACAT GGTGGACGGA GGGTAGCTAT CTTACGAGAC GCTGAATTCT
+1001 ATGAACACAG AAAAGAGGAA CGCTGTRCCC GTGTTTGGGG GACAACATGT ACAAAACACC
+1061 CCCATATCAA AATGGTGATG GAAAGTGGG ACTGGCTGGT TGGTGGAGAC CTTCAGGTGC
+1121 TGGAGAAAAT AAGATGGAAT GATGGGCTGG ACCAATACCG TCTGACACCT CTGGAGCTCA
+1181 AACAGAAATG TAAAGAAATG AATGCTGATG CGGTGTTTGC ATTCCAGTTG CGCAATCCTG
+1241 TCCACAATGG CCATGCCCTG TTGATGCAGG ACACCTGCCG CAGGCTCCTA GAGAGGGGCT
+1301 ACAAGCACCC GGTCCTCCTA CTACACCCTC TGGGCGGCTG GACCAAGGAT GACGATGTGC
+1361 CTCTAGACTG GCGGATGAAG CAGCACGCGG CTGTGCTCGA GGAAGGGGTC CTGGATCCCA
+1421 AGTCAACCAT TGTTGCCATC TTTCCGTCTC CCATGTTATA TGCTGGCCCC ACAGAGGTCC
+1481 AGTGGCACTG CAGGTCCCGG ATGATTGCGG GTGCCAATTT CTACATTGTG GGGAGGGACC
+1541 CTGCAGGAAT GCCCCATCCT GAAACCAAGA AGGATCTGTA TGAACCCACT CATGGGGGCA
+1601 AGGTCTTGAG CATGGCCCCT GGCCTCACCT CTGTGGAAAT CATTCCATTC CGAGTGGCTG
+1661 CCTACAACAA AGCCAAAAAA GCCATGGACT TCTATGATCC AGCAAGGCAC AATGAGTTTG
+1721 ACTTCATCTC AGGAACTCGA ATGAGGAAGC TCGCCCGGGA AGGAGAGAAT CCCCCAGATG
+1781 GCTTCATGGC CCCCAAAGCA TGGAAGGTCC TGACAGATTA TTACAGGTCC CTGGAGAAGA
+1841 ACTAAGCCTT TGGGTCCAGA GTTTCTTTCT GAAGTGCTCT TTGATTACCT TTTCTAT=TT
+1901 TATGATTAGA TGCTTTGTAT TAAATTGCTTCTCA//(SEQ. ID. NO.:1).

Preferably, the nucleic acid segment encoding a human PAPS synthetase, specifically PAPSS2, comprises a nucleotide sequence defining an open reading frame within SEQ. ID. NO.:1 that extends from nucleotide position +1 through +1845 (SEQ. ID. NO.:9).

The orthologous murine Papss2 gene is located in the bm region of mouse chromosome 19, within a 0.7 cM interval near marker D19Mit13. (See, FIG. 2; ul Haque, M. F., et al. [1998]). The cloned murine Papss2 nucleotide sequence is the following (GenBank accession AF085144; transcriptional start site [underlined] commences at position +1):

-60 GTATTCTCAA CATCAGATAT CATGTCTGG AGGAAGTTAC CTAAACTCTG AAGAATTATC
+1 <u>A</u>TGTCTGCAA ATTTCAAAAT GAACCATAAA AGAGACCAGC AAAAATCCAC CAATGTGGTC
+61 TACCAGGCCC ATCATGTGAG CAGGAACAAG AGAGGACAAG TGGTTGGAAC CAGGGAGGA
+121 TTCCGAGGAT GTACCGTGTG GCTAACAGGT CTCTCTGGTG CTGGGAAAAC AACCATAAGC
+181 TTTGCTTTGG AAGAGTACCT TGTATCTCAC GCCATCCCAT GTTACTCCCT GGATGGGGAC
+241 AATGTCCGTC ATGGCCTTAA TAAGAACCTG GGATTCTCTG CCGGGGACCG AGAAGAGAAT
+301 ATCCGCCGGA TCGCGGAGGT GGCCAAGCTC TTTGCCGACG CCGGCCTGGT TTGCATCACC
+361 AGCTTTATCT CTCCTTTTGC AAAGGATCGT GAGAATGCCC GAAAAATCCA CGAATCAGCA
+421 GGACTCCCGT TCTTTGAGAT CTTTGTAGAT GCGCCTTTAA ATATCTGTGA AAGCCGAGAC
+481 GTAAAAGGAC TCTACAAACG AGCCCGAGCA GGAGAGATTA AAGGGTTTAC AGGCATCGAT
+541 TCTGACTATG AGAAACCTGA AACTCCAGAG TGTGTGCTGA AGACCAACTT GTCTTCAGTA
+601 AGCGACTGTG TGCAACAGGT GGTGGAACTT TTGCAGGAGC AGAACATTGT ACCCACACC
+661 ACCATCAAAG GCATCCACGA ACTCTTTGTG CCAGAAAACA AAGTCGATCA AATCCGAGCT
+721 GAGGCAGAGA CTCTCCCATC ACTACCAATT ACCAAGCTGG ATCTGCAGTG GGTGCAGATT
+781 CTGAGTGAAG GCTGGGCCAC TCCCCTCAAA GGCTTTATGC GGGAGAAGGA ATACTTGCAA
+841 ACTCTACACT TCGACACTCT ACTGGACGAT GGAGTCATCA ACATGAGTAT TCCCATTGTA
+901 TTGCCCGTTT CTGCGGATGA CAAGGCACGG CTCGAAGGGT GCAGCAAATT TGCCTTGATG
+961 TACGAAGGTC GGAGGGTCGC TCTATTACAG GACCCTGAAT TCTATGAGCA TAGGAAAGAG
+1021 GAGCGTTGTT CTCGTGTGTG GGGAACAGCC ACTGCAAAGC ACCCCCATAT CAAAATGGTG
+1081 ATGGAAAGTG GGGACTGGCT TGTTGGTGGA GACCTACAGG TGCTAGAGAG AATAAGGTGG
+1141 GACGATGGGC TGGACCAATA CCGCCTTACG CCTCTGGAAC TCAAACAGAA GTGTAAAGAC
+1201 ATGAATGCTG ATGCCGTGTT TGCATrCCAG TTGCGCAATC CTGTCCACAA TGGTCATGCC
+1261 CTCCTGATGC AGGACACCCG CCGCAGGCTC CTGGAGAGGG GTTACAAGCA CCCAGTCCTC
+1321 CTGCTCCACC CTCTTGGGGG CTGGACCAAG GACGATGACG TACCTCTGGA ATGGAGGATG
+1381 AAACAGCATG CAGCTGTACT GGAGGAAAGG GTCCTGGATC CCAAGTCAAC TATTGTTGCC
+1441 ATCTTTCCAT CTCCTATGTT ATACGCTGGT CCCACAGAGG TCCAGTGGCA TTGCAGATGC
+1501 CGGATGATTG CAGGAGCCAA TTTCTACATT GTGGGTAGGG ATCCCGCAGG AATGCCCCAT
+1561 CCTGAGACAA AGAAAGACCT ATATGAACCC ACCCACGGGG GCAAGGTCTT GAGTATGGCC
+1621 CCTGGCCTTA CCTCTGTGGA AATAATTCCG TTCCGAGTGG CTGCCTACAA TAAAATTAAA
+1681 AAGGCCATGG ACTTTTATGA TCCAGCAAGG CACGAGGAGT TTGACTTCAT CTCAGGAACT
+1741 CGCATGAGGA AGCTCGCCCG GGAAGGAGAA GATCCCCCAG ATGGCTTCAT GGCCCCGAAA
+1801 GCGTGGAAAG TGTTGACAGA TTACTACAGG TCTCTGGAGA AGACCAACTA GGTGCTCCTG
+1861 GCTCTGGCTT CTTCCTCAAG TGCTCTCTGA CGATTTTTTT TTTCTATTTT TGTGATTTAG
+1921 CTGCTCTGTA TCCAATTGCA//(SEQ. ID. NO.:2).

Preferably, the nucleic acid segment encoding a murine PAPS synthetase, specifically Papss2, comprises a nucleotide sequence defiing an open reading frame within SEQ. ID. NO.:2 that extends from nucleotide position +1 through +1851 (SEQ. ID. NO.:10).

In other embodiments, the nucleic acid segment has a nucleotide sequence complementary to SEQ. ID. NOS.:1, 2, 9, or 10, or comprises a degenerate coding sequence of any of these. Alternatively, the present nucleic acid segment is a gene-specific fragment of SEQ. ID. NOS.:1, 2, 9 or 10, or a gene-specific fragment of a complementary sequence or degenerate coding sequence. Gene-specific fragments are nucleic acid segments having a contiguous nucleotide sequence that is specific to PAPSS2 or Papss2, respectively. For example, a gene-specific fragment of SEQ. ID. NO.:1 is SEQ. ID. NO.:9, and a gene-specific fragment of SEQ. ID. NO.:2 is SEQ. ID. NO.:10. The skilled artisan can readily determine other gene-specific fragments by conducting a sequence similarity search of a genomics data base, such as the GenBank database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine server. (E.g., Altchul, S. F., et al., *Gapped BLAST and PSI-BLAST: a new generation of protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996]; Altschul, S. F., et al., *Basic local alignment search tool*, J. Mol. Biol. 215(3):403–10 [1990]). Preferably, a gene specific fragment is at least 5 to 30 contiguous nucleotides long, more preferably at least 6 to 15 contiguous nucleotides long, and most preferably at least 7 to 10 contiguous nucleotides long. Embodiments of the isolated polynucleotide or nucleic acid construct of the present invention include nucleic acid segments comprising RNA, DNA, or chimeric RNA/DNA.

RNA segments include messenger RNA encoding an PAPSS2 or Papss2 protein, or a degenerate coding sequence, or a RNA sequence complementary to any of these. A complementary RNA segment can be an antisense RNA or a catalytic RNA sequence, such as a "hairpin" or "hammerhead" ribozyme, with a recognition sequence complementary to a gene-specific fragment of SEQ. ID. NOS.:1, 2, 9 or 10, or a degenerate coding sequence of any of these.

Other embodiments of the isolated polynucleotide or nucleic acid construct include nucleic acid segments of DNA. In some embodiments, the DNA segment encoding a PAPSS2 or Papss2 protein is operatively linked to a promoter sequence. The promoter sequence can be an autologous PAPSS2 or Papss2 promoter sequence. Alternatively, in a nucleic acid construct of the present invention, any suitable promoter sequence can be used, including an autologous promoter, a promoter from a heterologous human or non-human PAPS synthetase gene (e.g., PAPSS1 or Papss1 promoters), or a predetermined promoter sequence from any other human or non-human gene. Useful promoter sequences include constitutive promoters, such as, but not limited to, cytomegalovirus (CMV) promoter, or inducible promoters, such as, but not limited to, the human C-reactive protein (CRP) promoter (e.g., Kanzler, S., et al., *TGF-beta1 in liver fibrosis: an inducible transgenic mouse model to study liver fibrogenesis*, Am. J. Physiol. 276(4Pt 1):G1059–68 [1999]), or the insulin-like growth factor (IGF-I) promoter (e.g., Meton I., et al., *Growth hormone induces insulin-like growth factor-I gene transcription by synergistic action of STAT5 and HNF-1alpha*, FEBS Lett. 444(2–3):155–59 [1999]). Useful promoters include those that promote transcription in cells of diverse tissues, such as, but not limited to, an insulin receptor (IR) gene promoter (e.g., Tewari, D. S., et al., *Characterization of the promoter region and 3′ end of the human insulin receptor gene*, J. Biol. Chem. 264(27):16238–45 [1989]); growth hormone receptor (GHR) P2 or P3 promoters (e.g., Jiang, H., et al., *Isolation and characterization of a novel promoter for the bovine growth hormone receptor gene*, J. Biol. Chem. 274 (12):7893–900 [1999]); or a leptin promoter (e.g., Chen, X. L., et al., *Analysis of a 762-bp proximal leptin promoter to drive and control regulation of transgene expression of growth hormone receptor in mice*, Biochem. Biophys. Res. Commun. 262(1):187–92 [1999]).

Also useful for various applications are tissue-selective promoters, i.e., promoters from which expression occurs preferentially in cells of a particular kind of tissue, compared to one or more other types of tissue. These include, cartilage-selective promoters for expression in chondrocytes, for example, an osteocalcin (OC) promoter (e.g., Newberry, E. P., et al., *The RRM domain of MINT, a novel Msx2 binding protein, recognizes and regulates the rat osteocalcin promoter*, Biochemistry 38(33):10678–90 [1999]); a SOX9 promoter, aggrecan gene promoter (AGC1), or collagen oligomeric matrix protein (COMP) gene promoter (e.g., Kanai Y. & Koopman, P., *Structural and functional characterization of the mouse Sox9 promoter: implications for campomelic dysplasia*, Hum. Mol. Genet. 8(4):691–96 [1999]; Newton et al., *Characterization of human and mouse cartilage oligomeric matrix protein*, Genomics 24:435–39 [1994]); or a promoter from a collagen gene, such as, but not limited to promoters for COL2A1, COL9A1, or COL10A1. (e.g., Ganguly, A., et al., *Targeted insertions of two exogenous collagen genes into both alleles of their endogenous loci in cultured human cells: the insertions are directed by relatively short fragments containing the promoters and the 5′ ends of the genes*, Proc Natl Acad Sci USA 91(15):7365–9 [1994]; Dharmavaram, R. M., et al., *Detection and characterization of Sp1 binding activity in human chondrocytes and its alterations during chondrocyte dedifferentiation*, J. Biol Chem 272(43):26918–25 [1997]; Zhou, G., et al., *Three high mobility group-like sequences within a 48-base pair enhancer of the Col2a1 gene are required for cartilage-specific expression in vivo*, J. Biol Chem 273(24): 14989–97 [1998]; Seghatoleslami, M. R., et al., *Differential regulation of COL2A1 expression in developing and mature chondrocytes*, Matrix Biol 14(9):753–64 [1995]; Lefebvre, V., et al., *An 18-base-pair sequence in the mouse proalpha1(II) collagen gene is sufficient for expression in cartilage and binds nuclear proteins that are selectively expressed in chondrocytes*, Mol Cell Biol 16(8): 4512–23 [1996]; Zhou, G., et al., *A 182 bp fragment of the mouse pro alpha 1(II) collagen gene is sufficient to direct chondrocyte expression in transgenic mice*, J. Cell Sci, 108(Pt 12):3677–84 [3677–84]; Mukhopadhyay, K., et al., *Use of a new rat chondrosarcoma cell line to delineate a 119-base pair chondrocyte-specific enhancer element and to define active promoter segments in the mouse pro-alpha 1(II) collagen gene*, J. Biol Chem 270(46):27711–9 [1995]; Vikkula, M., et al., *Structural analysis of the regulatory elements of the tyupe-II procollagen gene. Conservation of promoter and first intron sequences between human and mouse*, Biochem J 285(Pt 1):287–94 [1992]; Beier, F., et al., *Localization of silencer and enhancer elements in the human type X collagen gene*, J Cell Biochem 662(2):210–8 [1997]; Thomas, J. T., *Sequence comparison of three mammalian type-X collagen promoters and preliminary functional anaysis of the human promoter*, Gene 160(2):291–6 [1995]; Apte, S. S., *Characterization of the mouse type X collagen gene*, Matrix 13(2):165–79 [1993]). A cartilage-derived retinoic acid-sensitive protein (CD-RAP) gene promoter is also useful for cartilage-selective expression by chondrocytes. (e.g., Xie, W. F., et al., *Transactivation of the mouse cartilage derived retinoic acid-sensitive protein gene by Sox9*, J. Bone Miner. Res. 14(5):757–63 [1999]).

For liver-selective expression in hepatocytes, useful promoter sequences include, an albumin gene promoter (e.g., Pastore, L., et al., *Use of a liver-specific promoter reduces immune response to the transgene in adenoviral vectors*, Hum. Gen. Ther. 10(11):1773–81 [1999]); a CYP7A or CYP7A1 promoter (e.g., Nitta, M., et al., *CPF: an orphan nuclear receptor that regulates liver-specific expression of the human cholesterol 7alpha-hydroxylase gene*, Proc. Natl. Acad. Sci. USA 96(12):6660–65 [1999]; Chen, J., et al., *Hepatocyte nuclear factor 1 binds to and transactivates the human but not the rat CYP7A1 promoter*, Biochem. Biophys. Res. Commun. 260(3):829–34 [1999]); a GHR P1 promoter (e.g., Zou, L., et al., *Isolation of a liver-specific promoter for human growth hormone receptor gene*, Endocrinology 138(4):1771–74 [1997]; Jiang, H., et al. [1999]; Adams, T. E., *Differential expression of growth hormone receptor messenger RNA from a second promoter*, Mol. Cell Endocrinol. 108(1–2):23–33 [1995]); or a thrombin-activatable fibrinolysis inhibitor (TAFI) promoter (e.g., Boffa, M. B., et al., *Characterization of the gene encoding human TAFI [thrombin-activatable fibrinolysis inhibitor; plasma procarboxypeptidase B]*, Biochemistry 38(20): 6547–58 [1999]).

For hematopoietic tissue-selective expression in hematopoietic precursor cells, useful promoters include a cyclin A1 promoter (e.g., Müller, C., et al., *Cloning of the cyclin A1 genomic structure and characterization of the promoter region*, J. Biol. Chem. 276(16):11220–28 [1999]); a CD34 promoter (e.g., Burn, T. C., et al., *Hematopoietic stem cell specific gene expression*, U.S. Pat. No. 5,556,954); or an integrin alphaIIb promoter (e.g., Wilcox, D. A., et al., *Integrin alphaIIb promoter-targeted expression of gene products in megakakyocytes derived from retrovirus-transduced human hematopoietic cells*, Proc. Natl. Acad. Sci. USA 96(17):9654–59 [1999]).

The foregoing examples of useful promoter sequences are not an exhaustive list, but are merely illustrative of the promoters available to the skilled artisan in practicing the present invention.

For purposes of the present invention, "operatively linked" means that the promoter sequence, is located directly upstream from the PAPSS2 or Papss2 coding sequence, which is in reading frame, and that both sequences are oriented in a 5' to 3' manner, forming a transcriptional unit, such that transcription can take place in vitro in the presence of all essential enzymes, transcription factors, co-factors, activators, and reactants, under favorable physical conditions, e.g., suitable pH and temperature. This does not mean that, in any particular cell, conditions will favor transcription.

By way of example, transcription of the DNA sequence encoding a PAPSS2 protein produces mRNA transcript, which is translatable into PAPSS2 protein, or a functional fragment thereof. Thus, one benefit of the present invention is that the nucleic acid can be used in a genetic replacement therapy for humans to correct clinical disorders derived from defective endogenous expression of PAPSS activity. Such defective expression can result from, but need not result from, endogenous underexpression of functional PAPSS2 protein, in particular.

Other preferred embodiments of the present nucleic acid construct also include, operatively linked as part of the transcriptional unit, a reporter gene sequence encoding a reporter protein for facilitating the detection or selection of cells containing the present nucleic acid construct and expressing PAPSS2 or Papss2. Preferably, but not necessarily, the reporter gene encodes a fluorescent protein. Fluorescent proteins include green fluorescent protein (or enhanced green fluorescent protein), yellow fluorescent protein, blue fluorescent protein, a phycobiliprotein, such as phycoerythrin or phycocyanin, or any other protein which fluoresces under suitable wave-lengths of light. Another reporter gene suitable for some applications is a gene encoding a protein that can enzymatically lead to the emission of light from a substrate(s); for purposes of the present invention, such a protein is a "light-emitting protein." For example, a light-emitting protein includes proteins such as luciferase or apoaequorin.

Alternatively, the DNA segment encodes a PAPSS2 or Papss2 gene-specific antisense RNA, such as an antisense RNA that specifically hybridizes to PAPSS2 mRNA or Papss2 mRNA, preventing translation therefrom.

In another embodiment, the nucleic acid construct comprises a chimeric RNA/DNA, such as a chimeric RNA/DNA oligonucleotide. Such RNA/DNA chimers are useful, for example, in altering single nucleotide polymorphisms (SNPs) or other point mutations in an endogenous PAPSS2 gene sequence. For example, a SNP in PAPSS2 associated with encoding a truncated or otherwise dysfunctional PAPSS2 protein can be stably repaired using a chimeric RNA/DNA oligonucleotide of the present invention.

In other embodiments, the nucleic acid construct is a probe or primer sequence. The inventive probe is a labeled polynucleotide that is useful in hybridization assays, such as Southern, Northern, or fluorescence in situ (FISH) hybidizations, for detecting the presence in a sample of polynucleotides having a gene-specific PAPSS2 or Papss2 sequence. The probe is fully complementary to SEQ. ID. NOS.:1, 2, 9, or 10, or is complementary to a gene-specific fragment of any of these. The suitable labels for a probe are typically radioisotopes or fluorogens incorporated into or covalently linked to the polynucleotide by methods known in the art, and are detectable by conventional radiation or fluorescence detecting methods.

The primer of the present invention is an oligonucleotide sequence that is useful in amplifying a nucleic acid segment from a sample that defines a nucleotide sequence specific to PAPSS2 or Papss2 by known methods of PCR, including RT-PCR. The primer is preferably 15 to 30 nucleotides long, and most preferably 17 to 22 nucleotides long, but primers as short as 7 contiguous nucleotides may be useful for some gene-specific sequences. (E.g., Vincent, J., et al., *Oligonucleonucleotides as short as 7-mers can be used for PCR amplification*, DNA Cell Biol. 13(1):75–82 [1994]).

Examples of useful oligonucleotide primer sequences for amplifying PAPSS2-specific nucleic acid segments include primer sequences comprising:

5'-TGGACCAAGGATGACGATGT-3' (SEQ. ID. NO.:3; forward primer);

5'-CGGAAAGATGGCAACAATGG (SEQ. ID. NO.:4; reverse primer);

5'-CTGGTGCTGGAAAAACAACG-3' (SEQ. ID. NO.:5; forward primer);

5'-TGCGAATGGAGAAATAAAGCTG (SEQ. ID. NO.:6; reverse primer);

5'-GCCAGCCAGCATGTCGGGGAT-3' (SEQ. ID. NO.:11; forward primer);

5'-ACCTGAAACTCCTGAGCGTGTGCT-3' (SEQ. ID. NO.:12; forward primer);

5'-GATGTGCCTCTAGACTGGCGG-3' (SEQ. ID. NO.:13; forward primer);

5'-GAGCACTTCAGAAAGAAACTCTGG-3' (SEQ. ID. NO.:14; reverse primer);

5'-CATCCGCCAGTCTAGAGGCAC-3' (SEQ. ID. NO.:15; reverse primer);

5'-AGGTGTCAGACGGTATTGGTC-3' (SEQ. ID. NO.:16; reverse primer);
5'-GTCACTCACTGTGGACAAATTGG-3' (SEQ. ID. NO.:17; reverse primer);
5'-CACCTCAGCAATCCGGCGGAT-3' (SEQ. ID. NO.:18; reverse primer);or
5'-GCATGTCCAGACAGACACCAC-3' (SEQ. ID. NO.:28; reverse primer), but a complementary nucleotide sequence, or a gene-specific fragment of any of these is also useful; also useful are PAPSS2-specific primer sequences that overlap any of the aforementioned primer sequences at 5 or more contiguous nucleotide positions at their 5' or 3' end.

Useful primers for amplifying Papss2-specific sequences include primer sequences comprising:
5'-TCTGGCACAAAGAGTTCGTG-3' [SEQ. ID. NO.:19; reverse primer]);
5'-GCCAGTTTGTAACCGAGTATTC-3' (SEQ. ID. NO.:20; forward primer);
5'-GCAATTGGATACAGAGCAGCTA-3' (SEQ. ID. NO.:21; reverse primer);
5'-GACAATGTCCGTCATGGCCTTA-3' (SEQ. ID. NO.:22; forward primer);
5'-ATrCCCATTGTATTGCCCGTT-3' (SEQ. ID. NO.:23; forward primer);
5'-AACGGCAATACAATGGGAAT-3' (SEQ. ID. NO.:24; reverse primer);
5'-GATAAAGCTGGTGATGCAAACC-3' (SEQ. ID. NO.:25; reverse primer);5'-CATGGGATGGCGTGAGATAC-3' (SEQ. ID. NO.:26; reverse primer); or
5'-CATAAGCTTTGCTTTGGAAGAGT-3' (SEQ. ID. NO.:27; forward primer); but a complementary nucleotide sequence, or a gene-specific fragment of any of these is also useful, also useful are Papss2-specific primer sequences that overlap any of the aforementioned primer sequences at 5 or more contiguous nucleotide positions at their 5' or 3' end.

The present invention also relates to a pair of oligonucleotide primers (i.e., a primer set) comprising at least one forward and at least one reverse oligonucleotide primer, which together are capable of producing detectable nucleic acid amplification products from the 5' and 3' ends of a PAPSS2 or Papss2 nucleic acid template in a PCR- or RT-PCR-based nucleic acid amplification method.

In some embodiments, the amplification products that the pair of primers can amplify include nucleic acid amplification products comprising (SEQ. ID. NO.:1) or (SEQ. ID. NO.:9); a nucleotide sequence complementary to either of those; or a PAPSS2 gene-specific fragment of any of these. Examples of this embodiment of the inventive pair of oligonucleotide primers include pairs containing a forward primer having a nucleotide sequence comprising (SEQ. ID. NOS.:3, 5, or any of 11–13), a complementary nucleotide sequence, a gene-specific fragment of either of these, or a nucleotide sequence overlapping at 5 or more contiguous nucleotide positions any sequence of those aforementioned at its 5' or 3' end; and containing a reverse primer having a nucleotide sequence comprising (SEQ. ID. NO.:4, 6, 14–18, or 28), a complementary nucleotide sequence, a gene-specific fragment of either of these; or a nucleotide sequence overlapping at 5 or more contiguous nucleotide positions any sequence of those aforementioned at its 5' or 3' end. For example, useful oligonucleotide primer pairs for amplifying a PAPSS2 gene sequence include (SEQ. ID. NO.:3 and 4) or (SEQ. ID. NO.:5 and 6).

In other embodiments, the amplification products that the pair of oligonucleotide primers can amplify include nucleic acid amplification products having (SEQ. ID. NO.:2) or (SEQ. ID. NO.:10); a nucleotide sequence complementary to either of those; or a Papss2 gene-specific fragment of any of these. Examples of this embodiment of the inventive primer pair include pairs containing a forward primer having a nucleotide sequence comprising (SEQ. ID. NO.:20, 22, 23, or 27), a complementary by nucleotide sequence, a gene-specific fragment of either of these, or a nucleotide sequence overlapping at 5 or more contiguous nucleotide positions any sequence of those aforementioned at its 5' or 3' end; and containing a reverse primer having a nucleotide sequence comprising (SEQ. ID. NOS.:19, 21, or any of 24–26), a complementary nucleotide sequence, a gene-specific fragment of either of these; or a nucleotide sequence overlapping at 5 or more contiguous nucleotide positions any sequence of those aforementioned at its 5' or 3' end.

Other embodiments of the inventive nucleic acid construct include those in which, cloned into an expression vector, is a DNA segment encoding a PAPSS2 or Papss2 protein, operatively linked with any suitable promoter sequence, including a human PAPSS2 promoter, a promoter from another human or non-human PAPS synthetase gene (e.g., PAPSS1, Papss1, or Papss2 promoters), or a predetermined promoter sequence from any other human or non-human gene, as described above. Suitable vector systems include, but are not limited to, viral vectors, for example, adenoviruses, adeno-associated viruses, retroviruses such as human immune-deficiency virus, other lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of cells and mixtures thereof. All of the above viruses may require modification to render them non-pathogenic or less antigenic. Other known vector systems, however, are also suitable for containing the DNA segment.

The present invention also relates to a genetically modified vertebrate cell containing the nucleic acid construct of the present invention, regardless of the method by which the construct was introduced into the cell. Embodiments include cartilage-forming cells, such as chondrocytes, and liver cells, such as hepatocytes, as well as cells derived from other tissues such as, colon, lung, placenta, aortic or other vascular endothelium, bone marrow, or heart.

If the nucleic acid construct includes a fluorescent reporter gene, as described above, the genetically modified cells of the present invention can be detected, isolated or selected from unmodified cells with the aid of, for example, a flow-activated cell sorter (FACS), set at the appropriate wavelength(s), or using conventional microscopic technology.

In particular applications involving a genetically modified cell that expresses additional xenogeneic genes from any promoter, this expression may be linked to a reporter gene that encodes a different fluorescent or light-emitting protein from the reporter gene linked to PAPSS2 or Papss2 expression. Thus, multiple reporters fluorescing or emitting at different wavelengths can be chosen and cell selections based on the expression of multiple traits can be made.

Gene delivery to the cell is by any suitable method including in vivo and in vitro gene delivery methods. (E.g., D. T. Curiel et al., U.S. Pat. Nos. 5,521,291 and 5,547,932). Typically, gene delivery involves exposing a cell to a gene delivery mixture that includes preselected genetic material together with an appropriate vector, mixed, for example, with an effective amount of lipid transfecting agent (lipofection). The amount of each component of the mixture is chosen so that gene delivery to a specific species of cell is optimized. Such optimization requires no more than routine experimentation. The ratio of DNA to lipid is broad, preferably about 1:1, although other proportions may also be utilized depending on the type of lipid agent and the DNA utilized. This proportion is not crucial. Other well known gene delivery methods include electroporation or chemical methods. (E.g., M. Ostresh, *No barriers to entry: transfection tools get biomolecules in the door*, The Scientist 13(11) :21–23 [1999]).

"Gene delivery agent", as used herein, means a composition of matter added to the genetic material for enhancing the uptake of exogenous DNA segment(s) into a vertebrate cell. The enhancement is measured relative to the uptake in the absence of the gene delivery agent. Examples of gene delivery agents include adenovirus-transferrin-polylysine-DNA complexes. These complexes generally augment the uptake of DNA into the cell and reduce its breakdown during its passage through the cytoplasm to the nucleus of the cell.

Other preferred gene delivery agents include Lipofectin®, DMRIE C, Cellfectin® or Lipofectamine (Life Technologies), LipoTAXI (Stratagene), Superfect or Effectene (Qiagen). Although these are not as efficient gene delivery agents as viral agents, they have the advantage that they facilitate stable integration of xenogeneic DNA sequence into the vertebrate genome, without size restrictions commonly associated with virus-derived gene delivery agents. A virus, or transfecting fragment thereof, can be used to facilitate the delivery of the genetic material into the cell. Examples of suitable viruses include adenoviruses, adeno-associated viruses, retroviruses such as human immune-deficiency virus, other lentiviruses, such as Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of cells and mixtures thereof. All of the above viruses may require modification to render them non-pathogenic or less antigenic. Other known vector systems are also useful.

The present invention also relates to genetically modified non-human vertebrates comprising the present genetically modified cells, for example, non-human primates, mice, rats, rabbits, gerbils, hamsters, canines, felines or other non-human mammals. Other vertebrates include birds such as chickens, turkeys, ducks, ostriches, emus, geese, guinea fowl doves, quail rare and ornamental birds, and the like. Broadly speaking, a genetically modified vertebrate is one that has had exogenous or foreign DNA permanently introduced into one or more of its cells, whether somatic or germ cells.

The present invention also relates to an isolated human PAPS synthetase protein comprising a polypeptide having an amino acid sequence of (SEQ. ID. NO.:7), i.e., the following contiguous amino acid residues, or an antibody binding fragment of the protein at least 6 amino acids long (amino acid residue 475 is in boldface):
MSGIKKQKTENQQKSTNVVYQAHHVS-
RNKRGQWGTRGGFRGCT VWLTGLSGAGKTTIS-
FALEEYLVSHAIPCYSLDGDNVRHGLN-
RNLGFSPGDREENIRR
AEVAKLFADAGLVCITSFISPFAK-
DRENARKIHESAGLPFFEIFVDAPLNICESRDV
KGLYKRARAGEIKGFTGIDSDYEKPET-
PERVLKTNLSTVSDCVHQVVELLQEQNIVPY
TIIKDIHELFVPENKLDHVRAEA-
ETLPSLSITKLDLQWVQVLSEGWATPLKGFMREKE
YLQVMHFDTLLDDGVINMSIPIVLPV-
SAEDKTRLEGCSKFVLAHGGRRVAILRDAEFY
EHRKEERCSRVWGTTCTKHPHIKMVMES-
GDWLVGGDLQVLEKIRWNDGLDQYRLTPLE
LKQKCKEMNADAVFAFQLRNPVHNGHA-
LLMQDTCRRLLERGYKHPVLLLHPLGGWTK D
DDVPLDWRMKQHAAVLEEGVLI)
PKSTIVAIFPSPMLYAGPTEVQWHCRSRMIAGANFY
IVGRDPAGMPHPETKDLYEPTHGGKVLS-
MAPGLTSVEIIPFRVAAYNKAKKAMDFYD PAR-
HNEFDFISGTRMLAREGENPPDGFMAPKAW
KVLTDYYRSEMDKN//(SEQ. ID. NO.:7).

This polypeptide sequence is encoded for example by (SEQ. ID. NO.:9), but is also encoded by other degenerate coding sequences.

In one embodiment, the PAPSS2 protein forms part of a PAPSS2 fusion protein along with a second predetermined polypeptide segment, which can have an amino acid sequence related or unrelated to (SEQ. ID. NO.:7). The PAPSS2 fusion protein includes a first PAPSS2 polypeptide segment comprising an amino acid sequence of (SEQ. ID. NO.:7), an enzymatically active fragment thereof, or a gene-specific antibody binding fragment of (SEQ. ID. NO.:7) at least 6 amino acids long; and a second predetermined polypeptide segment. The fusion protein is produced by known recombinant methods, and the second predetermined polypeptide sequence can be any desired polypeptide, for example, a known antigenic sequence, such as a specific goat, rabbit, or HLA antigen to which immunoreagents of commercially available immunoassay systems are directed. Thus, in some applications, conventional immunoassay systems can be used "off the shelf" to detect and quantify a PAPSS2 fusion protein by detecting the second polypeptide sequence.

In other applications, for example in protein therapy for the treatment of osteoarthritic disorders related to deficient enzymatic sulfation, the second polypeptide of the fusion protein is a polypeptide that allows the hybrid molecule to enter cells of a target tissue, for example, cartilage, liver, or platelets, whether in vitro or in vivo. For example, a second polypeptide can be chosen that infiltrates the cells of tissues, such as the human immunodeficiency virus (HIV) TAT protein (Schwarze, S. R., et al., *In vivo protein transduction: delivery of a biologically active protein into the mouse*, Science 285:1569–72 [1999]), and once within the cells, the PAPSS2 polypeptide segment of the fusion protein becomes enzymatically active in the sulfation pathway within the cells.

The present invention also relates to an isolated murine Papss2 protein comprising an amino acid sequence of (SEQ. ID. NO.:8), i.e., the following contiguous amino acid residues, or an antibody binding fragment of the protein at least 6 amino acids long:
MSANFKMNHKRDQQKSTNVVYQAHHVS-
RNKRGQVVGTRGGFRGC TVWLTGLSGAGKTTIS-
FALEEYLVSHAIPCYSLDGDN-
VRHGLNKNLGFSAGDREENIR
RIAEVAKLFADAGLVCITSFISPFAK-
DRENARKIHESAGLPFFEIFVDAPLNICESRD VKG-
LYKRARAGEIKGFTGIDSDYEKPET-
PECVLKTNLSSVSDCVQQVVELLQEQNIVP
HTTIKGIHELFVPENKVDQIRAEA-
ETLPSLPITKLDLQWVQILSEGWATPLKGFMREK
EYLQTLHFDTILDDGVINMSIPIV- LPVSADDKARLEGCSKFALMYEGRRVALLQDPEF
YEHRKEERCSRVWGTATAKHPHIKM-
VMESGDWLVGGDLQVLERIRWDDGLDQYRLTP L
ELKQKCKDMNADAVFAFQLRNPVHNGHA-
LLMQDTRRRLLERGYKHPVLLLHPLGGWT K
DDDVPLEWRMKQHAAVLEERVLDPKSTI-
VAIFPSPMLYAGPTEVQWHCRCRMIAGANF
YIVGRDPAGMPBPETKKDLYEPTEGGKV-
LSMAPGLTSVEIIPFRVAAYNKIKKAMDFY DPAR-
HEEFDFISGTRMRKLARGEDPPDGPMAPKA
KAWKVLTDYYRSEMDKTNh//(SEQ. ID. NO.:8).

This polypeptide sequence is encoded for example by (SEQ. ID. NO.:10), but is also encoded by other degenerate coding sequences.

In one embodiment, the Papss2 protein forms part of a Papss2 fusion protein along with a second predetermined polypeptide segment, which can have an amino acid sequence related or unrelated to (SEQ. ID. NO.:8). The Papss2 fusion protein includes a first Papss2 polypeptide segment comprising an amino acid sequence of (SEQ. ID. NO.:8) or a gene-specific antibody binding fragment thereof at least 6 amino acids long; and a second predetermined polypeptide segment. As above, the fusion protein is produced by known recombinant methods, and the second predetermined polypeptide sequence can be any desired polypeptide, for example, a known antigenic sequence, such as a specific goat, rabbit, or HLA antigen to which immunoreagents of commercially available immunoassay systems are directed. Thus, in some applications, conventional immunoassay systems can be used "off the shelf" to detect and quantify a Papss2 fusion protein by detecting the second polypeptide sequence.

The present invention also relates to an isolated antibody or antibody fragment that selectively binds a PAPS synthetase protein having an amino acid sequence of (SEQ. ID. NO.:7) or (SEQ.ID. NO.8), or selectively binds an antibody binding fragment of either of these at least 6 amino acids long. These are useful for detection and visualization of PAPSS2 or Papss2 proteins in various applications. The antibody or antibody fragment is raised against the PAPSS2 or Papss2 protein of the present invention. The antibody is raised in a mammal, from which it is isolated in serum, or is most preferably produced in a hybridoma cell line, by known methods, and is a monoclonal antibody. Antibody fragments of the present antibody are also useful; these include Fab', F(ab')2, or F(v) fragments that are produced by known methods, typically by pepsinization of whole antibody.

The present invention also relates to a method of diagnosing spondyloepimetaphyseal dysplasia in a human subject. The method involves amplifying a nucleic acid segment from a sample. The sample is derived from a human subject having at least one symptom of spondyloepimetaphyseal dysplasia, and the sample is of a bodily substance containing human nucleic acid of the subject. The nucleic acid segment defines a sequence from human chromosomal region 10q23–24, between microsatellite markers D10S1143 and D10S2470, to produce amplification products; and analyzing the amplification products for the presence of homozygosity for a variant allele of a PAPSS2 gene, the presence of homozygosity for the variant allele of the gene corroborating a diagnosis of spondyloepimetaphyseal dysplasia in the human subject.

Any bodily substance containing human nucleic acids from the subject may be sampled, collected, and/or transported for the purpose of practicing the method. A most preferred and convenient substance for sampling is blood. However, a sample of hair root, urine, amniotic fluid, chorionic villus biopsy, skin biopsy, vascular or oral epithelium, spinal fluid, or other biopsy sample of any tissue is also useful. The sample is derived from cultured human cells, cell-free extracts, or other specimens indirectly derived from a subject's body, as well as from substances taken directly from a subject's body. Samples may be stored before amplification and/or analysis by well known storage means that will preserve nucleic acids in an analyzable condition, such as quick freezing, or a controlled freezing regime, in the presence of a cryoprotectant, for example, dimethyl sulfoxide (DMSO), glycerol, or propanediol-sucrose. Samples may also be pooled before or after storage for purposes of amplifying their nucleic acids for analysis.

For purposes of the present invention "amplifying a nucleic acid segment" from a tissue sample of a subject "to obtain amplification products" encompasses any conventional means of amassing sufficient nucleic acid material for analysis. This includes, but is not limited to, amplification by conventional polymerase chain reaction methods (e.g., PCR, including RT-PCR). Alternatively, the practitioner can amplify the human subject's nucleic acids by in vitro cell culture and harvest of the subject's cultured cells, or by multiple sampling from the subject's tissues in vivo and pooling of multiple tissue samples from a subject. Nucleic acids thus "amplified," if they comprise a PAPSS2 gene or a gene-specific part thereof, are "amplification products" for purposes of the present invention.

In a most preferred embodiment of the present method, PCR is used for amplifying the subject's nucleic acids, particularly from a PAPSS2 gene. If PCR is used, any combination of oligonucleotide primers that will amplify nucleic acid sequences of a PAPSS2 gene, or parts thereof, can be employed. Most preferably, amplification of the subject's nucleic acids can be achieved using PAPSS2-specific oligonucleotide primers and primer pairs of the present invention, as described above. For example, useful primers comprise a nucleotide sequence of (SEQ. ID. NOS.:3–6, 11–18, or 28) or a PAPSS2-specific fragment of any of these at least 15 nucleotides long. In addition a sequence complementary to any of (SEQ. ID. NOS.:3–6, 11–18, or 28) or the PAPSS2-specific fragment, or any PAPSS2-specific nucleotide sequence at least 15 nucleotides long and overlapping at 5 or more contiguous nucleotide positions any of (SEQ. ID. NOS.:36, 11–18, or 28) at its 5' or 3' end, is a useful primer sequence. Examples of pairs of oligonucleotide primers useful for practicing the method include primer pairs comprising (SEQ. ID. NOS.:3 and 4) or (SEQ. ID. NOS. :5 and 6), but any of the present PAPSS2-specific primer pairs are useful.

In a preferred embodiment of the method of the present invention, nucleotide sequencing of PAPSS2 can be used to analyze the amplification products of the nucleic acids in a human subject's tissue sample to detect a variant allele in a PAPSS2 gene. A variant allele of PAPSS2 can be detected by any nucleotide sequencing means, for example conventional dideoxy sequencing or preferably by using a commercially available automated sequencer, then by comparing the subject's nucleotide sequences to other known human PAPSS2 sequences available in genomic sequence databases, such as GenBank.

In a most preferred embodiment of the present method that employs nucleotide sequencing, sequencing of PAPSS2 may be accomplished by using fluorescence-based single strand conformation polymorphism analysis (SSCP), a routine and reliable means of identifying point mutations, small insertions or deletions. (J. S. Ellison, *Fluorescence-based* mutation detection. *Single-strand conformation polymorphism analysis [F-SSCP]*, Mot Biotechnol. 5(1):17–31 [1996]; H. Iwahana et al., *Multiple fluorescence-based PCR-SSCP analysis using internal fluorescent labeling of PCR products*, Biotechniques 21(3):510–14, 516–19 [1996]; R. Makino et al., *F-SSCP: fluorescence-based polymerase chain reaction-single-strand conformation polymorphism [PCR-SSCP]*, PCR Methods Appl. 2(1):10–13 [1992]). An automated system may be used, such as an Applied Biosystems DNA sequencer, equipped with GENESCAN 672, Genetyper, or another appropriate analytical software package.

Optionally, high throughput analysis is achieved by PCR multiplexing techniques well known in the art. (E.g., Z. Lin et al., *Multiplex genotype determination at a large number of gene loci*, Proc. Natl. Acad. Sci. USA 93(6):2582–87 [1996]).

In another preferred embodiment of the present method, nucleotide sequencing is unnecessary for analyzing the amplification products. For example, heteroduplex analysis on high resolution gel matrices can be employed by the skilled practitioner to detect even single nucleotide polymorphisms. (M. T. Hauser et al., *Generation of co-dominant PCR-based markers by duplex analysis on high resolution gels*, Plant. J. 16(1):117–25 [1998]). The PCR/OLA procedure can be used for analyzing amplification products to detect SNPs in PAPSS2. (B. R. Glick and J. J. Pasternak, *Molecular Biotechnology: Principles and Applications of Recombinant DNA*, ASM Press, Washington, D.C., pp. 197–200 [1994]). Conformation-sensitive gel electrophoresis of amplification products can also be employed as a means of analysis by the skilled artisan in practicing the methods of the present invention. (A Markoff et al., *Comparison of conformation-sensitive gel electrophoresis and single strand conformation polymorphism analysis for detection of mutations in the BRCA1 gene using optimized conformation analysis protocols*, Eur. J. Genet. 6(2):145–50 [1998]).

A skilled practitioner will know that electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, the use of radionuclides, biotin, UV-absorbance or laser-induced fluorescence. (K. Keparnik et al., *Fast detection of a (CA)18 microsatellite repeat in the Ig E receptor gene by capillary electrophoresis with laser-induced fluorescence detection*, Electrophoresis 19(2); 249–55 [1998]; H. Inoue et al., *Enhanced separation of DNA sequencing products by capillary electrophoresis using a stepwise gradient of electric field strength*, J. Chromatogr. A. 802(1):179–84 [1998]; N. J. Dovichi, *DNA sequencing by capillary electrophoresis*, Electrophoresis 18(12–13): 2393–99 [1997]; H. Arakawa et al., *Analysis of single-strand conformation polymorphisms by capillary electrophoresis with laser induced fluorescence detection*, J. Pharm. Biomed. Anal. 15(9–10):1537–44 [1997]; Y. Baba, *Analysis of disease-causing genes and DNA-based drugs by capillary electrophoresis Towards. DNA diagnosis and gene therapy for human diseases*, J. Chromatgr B. Biomed. Appl. 687(2): 271–302 [1996]; K. C. Chan et al., *High-speed electrophoretic separation of DNA fragments using a short capillary*, J. Chromatogr B. Biomed. Sci. Appl. 695(1): 13–15 [1997]).

Any of diverse fluorescent dyes are optionally used to label primers or amplification products for ease of analysis, including but not limited to, fluorescein, SYBR Green I, YO-PRO-1, thiazole orange, Hex (i.e., 6-carboxy-2',4',7',4, 7-hexachlorofluoroscein), FAM (i.e., 6-carboxyfluoroscein), or TET (i.e., 4,7,2',7'-tetrachloro-6-carboxyfluoroscein). (E.g., J. Skeidsvoll and P. M. Ueland, *Analysis of double-stranded DNA by capillay electrophoresis with laser-induced fluorescence detection using the monomeric dye SYBR green I*, Anal. Biochem. 231(20):359–65 [1995]; H. Iwahara et al., *Multiple fluorescence-based PCR-SSCP analysis using internal fluorescent labeling of PCR products*, Biotechniques 21(30:510–14, 516–19 [1996]).

Analyzing the amplification products can also be done by means of restricting the amplification products with one or more restriction enzymes, for example HincII, followed by separation of the resulting fragments and analysis of fragment length or differential fragment migration in denaturing high-performance liquid chromatography (DHPLC) or gel electrophoresis, as above, including restriction-capillary electrophoresis. For example, this may be achieved by techniques known in the art, such as PCR-restriction fragment-SSCP, which can detect single base substitutions, deletions or insertions. (M. Tawata et al., *A mass screening device of genome by polymerase chain reaction-restriction fragment-single strand conformation polymorphism anaysis*, Genet. Anal. 12(3–4):125–27 [1996]; H. H. Lee et al., *Mutational analysis by a combined application of the multiple restriction fragment-single strand conformation polymorphism and the direct linear amplification DNA sequencing protocols*, Anal. Biochem. 205(2);289–93 [1992]).

Variant alleles of a PAPSS2 gene may be of any nucleotide sequence defining an open reading frame, or part thereof, that encodes PAPSS2 protein, or of any nucleotide sequence, or part thereof defining a regulatory region of a PAPSS2 gene. A PAPSS2 regulatory region may include, but is not limited to, a promoter region, an enhancer, a termination sequence, or any other nucleotide sequence, or part thereof that regulates the transcription of PAPSS2 protein. Any mutation or polymorphism in a PAPSS2 gene that results in a loss of PAPSS2 expression or a decrease in PAPSS2 functional activity relative to a normal activity range, or which could do so if it were not masked by the presence in vivo of a fully functional PAPSS2 allele or by another compensatory physiologic mechanism, are contemplated by the present invention.

For example, one variant allele of PAPSS2, characteristic of SEMD Pakistani-type, defines a stop codon instead of a serine codon corresponding to amino acid residue 475 of SEQ. ID. NO.:7, and results in synthesis of a truncated PAPSS2 protein 474 amino acids long. Homozygosity for this variant allele is associated with SEMD Pakistani-type in a human subject, and thus corroborates a diagnosis of SEMD Pakistani type.

However, detecting heterozygosity for a variant PAPSS2 allele is also useful, for genetic counseling purposes. Consequently, the present invention also relates to a method of identifying a human carrier of an heritable allele associated with spondyloepimetaphyseal dysplasia. As in the present method of diagnosing spondyloepimetaphyseal dysplasia, the method of identifying a carrier involves amplifying a nucleic acid segment from a sample derived from a human subject without symptoms of spondyloepimetaphyseal dysplasia, to produce amplification products. As described above, the sample is of a bodily substance containing human nucleic acid of the subject. The nucleic acid segment defines a sequence from human chromosomal region 10q23–24, between microsatellite markers D10S1143 and D10S2470. The amplification products are analyzed for the presence of a variant allele of a PAPSS2 gene, which is accomplished as described above. The presence of the variant allele of the gene identifies the human subject as a carrier of an heritable allele associated with spondyloepimetaphyseal dysplasia. A benefit of the present method of identifying a human carrier of an heritable allele associated with SEMD, is that couples in which one or both of the spouses is identified as a carrier of a SEMD-associated allele, can make more informed reproductive decisions.

The present invention also relates to a gene therapy method for treating a human subject having an osteoarthritic disorder that is caused or aggravated by deficient enzymatic sulfation activity. Examples include spondyloepimetaphyseal dysplasia, Stickler syndrome, spondyloepiphyseal dysplasia, and achondrogenesis; achondroplasia; chondrodysplasia; diastrophic dysplasia; the collagen oligomeric matrix protein (COMP) disorders such as pseudoachondroplasia and multiple epiphyseal dysplasia. In one embodiment, the method involves exposing, in vitro, one or more cells derived directly (e.g., biopsied) or indirectly (e.g., cultured) from a tissue of a human subject having at least one symptom of an osteoarthritic disorder caused or aggravated by deficient enzymatic sulfation activity to a gene delivery mixture comprising at least one gene delivery agent and a nucleic acid construct having a nucleic acid segment encoding a PAPS synthetase protein having an amino acid sequence of (SEQ. ID. NO.:7) or (SEQ. ID. NO.:8); causing the nucleic acid construct to be taken up by, and released into the cell(s), such that the nucleic acid construct is incorporated into the genome of the cell(s), whereby under appropriate physiological conditions expression of functional PAPS synthetase protein is enhanced in the cell(s), compared to unmodified cells of the same kind. The genetically modified cells are then implanted into the tissue of the human subject, where PAPS synthetase activity is thereby enhanced relative to pre-implantation, and at least one symptom associated with the osteoarthritic disorder in the subject is improved.

For purposes of treating symptoms of aberrant skeletal growth, the human subject is preferably a juvenile, and most preferably a prepubescent juvenile. However, for purposes of treating symptoms of joint degeneration associated with osteoartritic disorders, such as SEMD or chondrodysplasia, and for stabilizing the cartilage matrix, the human subject is any age. In one embodiment, the gene therapy method for treating an osteoarthritic disorder caused or aggravated by deficient enzymatic sulfation activity is directed to symptom(s) related to deficient sulfation activity that may arise in liver cells, e.g., hepatocytes, in platelets, or in vascular tissue, and these symptoms are treated in accordance with the method at any age, depending only on the practitioner's best estimation of the physiologic resilience of the individual patient in facing the stresses of the procedure.

These stresses are typically minimal, as cells can be obtained by pertcutaneous or laparoscopic biopsy. However, cells are also obtained by any other suitable surgical means or from a pre-existing culture derived from a tissue of the subject or other viable sample of the subject's cells. Implantation of the genetically modified cells is accomplished by conventional percutaneous, laparoscopic, stereotactic, or other surgical methods.

The method involves genetically modifying a cell(s) derived from a tissue of the subject. Preferably, but not necessarily, this is a cartilage-forming cell, such as a chondrocyte from an epiphyseal region. However, other cell types can also be genetically modified in accordance with the method to improve osteoarhritic symptoms that may be associated with other tissues, for example hepatocytes, platelets, or vascular endothelium. The cells, for example, chondrocytes, hepatocytes, hematopoietic precursor cells, or vascular endothelial cells, are obtained from an appropriate tissue, such as the epiphyses, joints, liver, bone marrow, or vascular tissue.

The cell(s) are genetically modified. This can be by any suitable gene delivery method as described above, preferably in vitro, for example by transfection, transduction, or electroporation, but in vivo methods of gene delivery are also contemplated. The cell(s) is exposed to a gene delivery mixture comprising at least one gene delivery agent, as described above, and a nucleic acid construct, preferably DNA, containing a nucleic acid segment encoding a PAPS synthetase protein having an amino acid sequence of (SEQ. ID. NO.:7), for example (SEQ. ID. NO.:9), or containing a nucleic acid segment encoding a PAPS synthetase protein having an amino acid sequence of (SEQ. ID. NO.:8), for example (SEQ. ID. NO.:10), operatively linked, in a transcriptional unit, to a predetermined promoter sequence that operates in the cell.

The nucleic acid construct that is used in the present gene therapy method optionally contains a reporter gene for convenient detection, isolation or selection of genetically modified cells expressing PAP synthetase protein from an exogenously supplied gene, as described above.

The construct is then taken up by and released into the cell, and is incorporated into the genome of the cell. Under appropriate physiological conditions, transcription of the PAPSS2 or Papss2 encoding region occurs, followed by translation, and thus, expression of PAPSS2 or Papss2 protein is enhanced in the cell, compared to unmodified cells of the same kind. With the cell(s) implanted in the tissue of the subject, one or more symptoms of the osteoarthritic disorder in the subject are thereby improved due to enhanced enzymatic sulfation in the tissue of biochemicals that require sulfation for bioactivity or have increased bioactivity in humans in a sulfated form.

Under some circumstances, the practitioner may deem it desirable to apply the present gene therapy method to a fetal subject that has been identified as being homozygous for a variant allele of a PAPSS2 gene by the present method of diagnosing spondyloepimetaphyseal dysplasia. In such instances, chondrocytes and stem cell precursors of chondrocytes can be obtained from fetal cartilage, can be genetically modified and re-implanted while the subject is in utero.

Another embodiment of the gene therapy method of the present invention involves a gene modification strategy employing a chimeric RNA/DNA otigonucleotide construct, particularly useful in repairing SNPs associated with a SEMD phenotype, such as the allele encoding a stop codon instead of serine at position 475 of (SEQ. ID. NO.:7) (e.g., "TAA" instead of "TCA" at nt. +1423 through +1425 of SEQ. ID. NO.:1; see FIG. 3), associated with SEMD Pakistani type. (E.g., Kren, B. T., et al., *Gene repair using chimeric RNA/DNA oligonucleotides*, Semin. Liver Dis. 19(1):93–104 [1999]; Alexeev, V. & Yoon, K., *Stable and inheritable changes in genotype and phenotype of albino melanocytes induced by an RNA-DNA oligonucleotide*, Nat. Biotechnol. 16(13):1343–46 [1998]; Cole-Strauss, A., et al., *Targeted gene repair directed by the chimeric RNA/DNA oligonucleotide in a mammalian cell free extract*, Nucleic Acids Res. 27(5):1323–30 [1999]; Xiang, Y., et al., *Targeted gene conversion in a mammalian CD34$^+$-enriched cell population using a chimeric RNA/DNA oligonucleotide*, J. Mol. Med. 75(11–12):829–35 [1997]; Cole-Strauss, A., et al., *Correction of the mutation responsible for sickle cell anemia by an RNA-DNA oligonucleotide*, Science 273 (5280):1386–89 [1996]; Yoon, K., et al., *Targeted gene correction of episomal DNA in mammalian cells mediated by a chimeric RNA.DNA oligonucleotide*, Proc. Natl. Acad. Sci. USA 93(5):2071–76 [1996]). Briefly, this gene modification strategy exploits the recombinogenicity of RNA-DNA hybrids and features the use of chimeric RNA/DNA oligonucleotides with hairpin capped ends that avoid destabilization or destruction by cellular helicases or exonucleases; an RNA/DNA oligonucleotide is designed so that it perfectly aligns with a specific genoric target sequence except for a single mismatched basepair, which is recognized by endogenous DNA repair systems that can then convert the SNP to a desired normal sequence.

In this embodiment, the cells are exposed to a nucleic acid construct that includes a chimeric RNA/DNA oligonucleotide. This chimeric RNA/DNA comprises a nucleic acid segment of a PAPSS2 gene comprising a nucleotide sequence of (SEQ. ID. NO.:9), (SEQ. ID. NO.:10), or a gene-specific fragment of either of these. The nucleic acid construct is taken up by, and released into, the cell, and the nucleotide sequence of the nucleic acid segment is incorporated into the genome of the cell, whereby expression of functional PAPS synthetase protein is enhanced in the cell. Under appropriate physiological conditions, transcription of the PAPSS2 or Papss2 encoding region occurs, followed by translation, and thus, expression of PAPS synthetase protein is enhanced in the cell, compared to unmodified cells of the same kind. The genetically modified cell(s) is then implanted into the tissue of the human subject, as described above. With the cell(s) implanted in the tissue of the subject, one or more symptoms of the osteoarthritic disorder in the subject are thereby improved due to enhanced enzymatic sulfation in the tissue of biochemicals that require sulfation for bioactivity or have increased bioactivity in humans in a sulfated form.

Thus, the gene therapy method provides a much needed way to improve or eliminate symptoms of aberrant skeletal growth or joint degeneration associated with osteoarthritic disorders such as SEMD. The method provides a way to improve symptoms resulting from deficient sulfation activity in other cell types, such as hepatocytes, platelets, or vascular epithelium, for example, abnormally long bleeding time.

The present invention is also related to a protein therapy method for treating a human subject having an osteoarthritic disorder. The osteoarthritic disorder is one that is caused or aggravated by deficient enzymatic sulfation activity, as described above. The method employs the inventive PAPSS2 fusion protein. The method involves exposing a cell(s) of a tissue of a human subject having the osteoarthritic disorder to a fusion protein comprising a first PAPSS2 polypeptide segment that comprises an amino acid sequence of (SEQ. ID. NO.:7), or an enzymatically active fragment thereof, and a second polypeptide segment capable of infiltrating the cell, whereby the fusion protein is taken up by the cell and the PAPSS2 polypeptide segment is enzymatically active within the cell. Exposing the cell(s) is preferably accomplished in vivo, for example by injecting or infusing the fusion protein into the subject. An example of a second polypeptide segment capable of infiltrating a diversity of cell types is an human immunodeficiency virus (HIV) TAT protein. (Schwarze, S. R, et al. [1999]). But a tissue-specific second polypeptide can also be used.

The skilled artisan is aware of suitable means of detecting an improvement in the subject's symptom(s) resulting from treatment by the inventive genetic or protein therapy methods. For example, a useful indicator of improvement in symptoms of aberrant skeletal growth is a comparison of the subject's growth rate over a period of months or years after treatment using the method, with the rate of growth before treatment. It is also useful to compare the subject's growth over time after treatment with standard growth curves or tables for humans of the same age and sex. Improvement in joint function, for example reduction in joint pain or enhanced joint movement, or joint appearance on x-ray, are useful indicators. Another useful indicator is improvement in platelet function, which is detected in normalized or shortened bleeding time for the subject.

Alternatively, biochemical or molecular methods are employed to detect improvement. For example, assays showing increased sulfation activity in a tissue biopsy sample(s) from the subject, such as in cartilage, liver, or blood samples and/or extracts, are useful in determining the effectiveness of the method. Commonly, such assays are based on direct measurement of in vivo and/or in vitro PAPS synthetase enzymatic activity or detecting the assimilation of sulfate into APS (i.e., sulfate activation assay) or into other sulfated metabolites, for example measuring the degree of sulfation of aggrecan side chains. Radiolabeled (e.g., $^{35}$S) sulfate and chromatographic separations are common tools used in such assay methods. Detection of PAPSS2-specific mRNA transcripts in tissue samples, using the probes or primers of the present invention, can also be employed as an indirect measure of improvement.

Alternatively, the nucleic acid construct that is used in the present gene therapy method can optionally contain in the transcriptional unit a reporter gene, as described above, for convenient detection of genetically modified cells expressing exogenous PAPSS2 in a tissue biopsy sample(s) from the subject.

The present invention is also related to a genetic testing kit for diagnosing SEMD in a human subject. The kit is an assemblage of materials for facilitating amplifying nucleic acids from a human subject comprising PAPSS2 nucleotide sequences and/or analyzing PAPSS2-derived amplification products. A genetic testing kit of the present invention comprises at least one oligonucleotide primer of the present invention and preferably comprises a pair of oligonucleotide primers of the present invention, together with instructions for the practice of the methods of the present invention. A most preferred embodiment of the genetic testing kit of the present invention comprises an inventive pair of oligonucleotide primers, as described above, for example (SEQ. ID. NOS.:3 and 4) or (SEQ. ID. NOS.:5 and 6). A preferred embodiment of the genetic testing kit of the present invention can incorporate an array of oligonucleotide primers specific for SNPs in human PAPSS2, preassembled in a "DNA chip" (or "gene chip") configuration for facilitating the amplifying of nucleic acids and the analyzing of amplification products. (E.g., J. G. Hacia et al., *Enhanced high density oligonucleotide array-based sequence analysis using modified nucleoside triphosphates*, Nucleic Acids Res. 26(2):4975–82 [1998]; R. W. Wallace, *DNA on a chip: serving up the genome for diagnostics and research*, Mol. Med. Today 3(9):384–89 [1997]; T. Pastinen et al., *Minisequencing: a specific tool for DNA analysis and diagnostics on oligonucleotide arrays*, Genome Res. 7(6):606–14 [1997]; M. T. Cronin et al., *Cystic fibrosis mutation detection by hybridization to light-generated DNA probe arrays*, Hum. Mutat. 7(3):244–55 [1996]; A. C. Pease et al., *Light-generated oligonucleotide arrays for rapid DNA sequence analysis*, Proc. Natl. Acad. Sci. USA 91(11):5022–26

[1994]; E. M. Southern et al., *Arrays of complementary oligonucleotides for analyzing the hybridization behaviour of nucleic acids*, Nucleic Acids Res. 22(8):1368–73 [1994]).

The present invention also relates to a kit for genetically modifying a vertebrate cell. The kit is a ready assemblage of materials or components for facilitating the genetic modification of a vertebrate cell. The kit includes a polynucleotide comprising a PAPSS2 sequence having SEQ. ID. NOS.:1, or a Papss2 sequence having SEQ. ID. NO.:2, a sequence complementary to either of these, or a degenerate coding sequence thereof (i.e., encoding SEQ. ID. NOS.:7 or 8), or a gene-specific fragment of any of these, as described herein with respect to the nucleic acid construct of the present invention. Preferably the polynucleotide includes a transcriptional unit that contains the human PAPSS2- or murine Papss2-encoding nucleic acid segment, operatively linked to a functional promoter sequence, and/or a reporter gene for facilitating detection, isolation, or selection of genetically modified cells from unmodified cells. The kit optionally contains a suitable gene delivery agent. The kit is particularly useful in practicing the gene therapy method for treating a human subject having an osteoarthritic disorder that is caused or aggravated by deficient enzymatic sulfation activity.

However, in several embodiments, the kit includes a DNA sequence encoding the PAPSS2 or Papss2 protein, or fragment thereof at least 6 amino acids long, in a sense or antisense orientation, as appropriate for a particular application. Alternatively, the kit includes a PAPSS2- or Papss2-specific chimeric RNA/DNA oligonucleotide, as described above. Some embodiments of the kit are configured for use in practicing the present method of treating a human subject having an osteoarthritic disorder, as described above.

The present invention also relates to a kit for practicing the inventive method of protein therapy for treating a human subject having an osteoarthritic disorder that employs the inventive PAPSS2 fusion protein, as described above. The kit contains a fusion protein comprising a first PAPSS2 polypeptide segment that comprises an amino acid sequence of (SEQ. ID. NO.:7), or an enzymatically active fragment thereof and a second polypeptide segment capable of infiltrating the cell, whereby the fusion protein is taken up by the cell and the PAPSS2 polypeptide segment is enzymatically active within the cell. An example of a second polypeptide segment capable of infiltrating cell(s) is an human immunodeficiency virus (HIV) TAT protein, which can infiltrate diverse cell types, but other polypeptide segments are also useful.

The materials or components assembled in the present kits for diagnosing SEMD or identifying a carrier of a heritable marker associated with SEMD and kits for genetically modifying a vertebrate cell or for protein therapy can be provided to the practitioner stored in any convenient and suitable ways that preserve their operability and utility. For example the components can be in dissolved, dehydrated, or lyophilized form; they can be provided at room, refrigerated or frozen temperatures. The kits of the present invention include instructions for using the materials or components effectively for their intended purpose(s).

It is contemplated that the polynucleotides, nucleic acid constructs, primers, primer pairs, and kits of the present invention can be used therapeutically to detect SEMD in patients with specific variant alleles of PAPSS2. These variant alleles can be targeted for gene therapy directed at repairing malfunctional PAPSS2 alleles or they may suggest specific chemotherapy directed to enhancing endogenous PAPS synthetase activity or may be directed to other metabolic targets in biochemical pathways mediated by PAPS synthetase activity.

The foregoing descriptions of the isolated polynucleotides, nucleic acid constructs, genetically modified cells and vertebrates, methods, and kits of the present invention are illustrative and by no means exhaustive. The invention will now be described in greater detail by reference to the following non-limiting examples.

EXAMPLES

Example 1

Methods

Genotyping. Synthetic oligonucleotide primers were obtained for genotyping in the SEMD family with polymorphic microsatellite markers from the CHLC Human Screening Set/Weber version 8 (Research Genetics). Additional markers were derived from a physical map of chromosome 10 (Gray, I. C., et al., *An integrated physical and genetic map spanning chromosome band 10q24*, Genomics 43:85–88 [1997]) and databases from the Whitehead Institute for Biomedical Research, the Cooperative Human Linkage Center, and Genethon.

Similar methods were used for analysis of microsatellite markers in the brachymorphic mice, using DNA samples from backcross animals recombinant in the bm region. (Rusiniak, M. E., et al., *Molecular markers near the mouse brachymorphic (bm) gene, which affects connective tissues and bleeding time*, Mamm. Genome 7:98–102 [1996]). Markers were derived from the Whitehead Institute for Biomedical Research mouse genetic and physical mapping database (http://www-genome.wi.mit.edu/cgi-bin/mouse/index).

Linkage Calculations. Two-point linkage analyses were conducted for eight markers in the region of D10S1143 (see FIGS. 1 and 2 and Table 1). LOD scores were calculated with the MLINK subroutine of the LINKAGE 5.1 package (Terwilliger, J. D. & Ott, J., *Handbook of human genetic linkage*, Baltimore:John Hopkins University Press [1994]) using a Pentium PC. Because of the computational problems introduced by extensive inbreeding and multiple generations with no genotyping or phenotyping data, the SEMD pedigree was divided into three separate sub-pedigrees. Individuals in the three nuclear families from the most recent generation, including each of their ancestors back to the founding couple as well as all inbreeding loops, were analyzed separately. The genotypes of each individual were analyzed only once.

SEMD was modeled as an autosomal recessive fully penetrant disease with an allele frequency of 0.0001. LOD scores were summed across the pedigrees. The LOD scores of $-\infty$ reflect recombinations within nuclear families for markers D10S2470 and D10S1753. Other markers did not recombine within the nuclear families, so that q=0.0 could not be ruled out for them, although parsimony indicates that recombination has probably occurred within the pedigree for each of these markers. The maximum LOD scores for markers D10S1143 and D10S2470 at q=0.01 were consistent with the results of the haplotype analysis. Because marker allele frequencies in the Pakistani population are unknown, for each marker, the allele frequencies were set at 1/N, where N was the number of observed alleles in the pedigree.

Radiation Hybrid Mapping. DNA from the Genebridge 4 Radiation Hybrid (RH) panel was obtained from Research Genetics. For the PAPSS2 gene, a 236 bp PCR product was amplified using primers 5'-CTGGTGCTGGAAAAACAACG-3' (SEQ. ID. NO.:5; forward primer) and 5'-TGCGAATGGAGAAATAAAGCTG-3' (SEQ. ID. NO.:6; reverse primer). RH data were submitted to the Whitehead server (http://www-genome.wi.mit.edu/cgi-bin/contig/rhmapper.p1) for placement on the RH map.

Computer Methods. BLAST searches (Altschul, S. F.,et al., Gapped BLAST and PSI-BLAST: *a new generation of protein search programs*, Nucleic Acids Res. 25:3389–3402 [1997]) and determinations of sequence homology were performed using the National Center for Biotechnology Information (http://www.ncbi.nlm.nih.gov/BLAST/) and Baylor College of Medicine (http://dot.imgen.bcm.tmc.edu:9331/seq-search/nucleic_acid-search.html) servers. The phenoytpic map of the mouse genome was accessed through the Mouse Genome Informatics server (http://www.informatics.jax.org), maintained by the Jackson Laboratory.

cDNA library analysis. To isolate the human PAPSS2 cDNA clones, oligonucleotide primers B (SEQ. ID. NO.:12, below) and E (SEQ. ID. NO.:15, below) were designed from the EST sequences identified by BLAST searching to amplify an 826 bp cDNA fragment by RT-PCR from human fetal cartilage RNA. The fragment was hybridized to plaques from a directional human fetal cartilage cDNA library constructed by Stratagene in the lambda ZAP2 vector (D. Krakow and D. Cohn, unpublished). Alternatively, a forward primer (SEQ. ID. NO.:11, below) and a reverse primer 5'-GCATGTCCAGACAGACACCAC-3' (SEQ. ID. NO.:28) were used to produce, from fetal cartilage RNA, a cDNA sequence 1940 base pairs long, including the entire PAPSS2 coding region and flanking regions, which nucleic acid segment was then used as a hybridization probe of the fetal cartilage cDNA library.

Primers used for sequence analysis of the cDNA clones were:
(A) 5'-GCCAGCCAGCATGTCGGGGAT-3' (SEQ. ID. NO.:11; forward primer);
(B) 5'-ACCTGAAACTCCTGAGCGTGTGCT-3' (SEQ. ID. NO.:12; forward primer);
(C) 5'-GATGTGCCTCTAGACTGGCGG-3' (SEQ. ID. NO.:13; forward primer);
(D) 5'-GAGCACTTCAGAAAGAAACTCTGG-3' (SEQ. ID. NO.:14; reverse primer);
(E) 5'-CATCCGCCAGTCTAGAGGCAC-3' (SEQ. ID. NO.:15; reverse primer);
(F) 5'-AGGTGTCAGACGGTATTGGTC-3' (SEQ. ID. NO.:16; reverse primer);
(G) 5'-GTCACTCACTGTGGACAAATTGG-3' (SEQ. ID. NO.:17; reverse primer); and
(H) 5'-CACCTCAGCAATCCGGCGGAT-3' (SEQ. ID. NO.:18; reverse primer).

The sequence of 3' end of the coding region of the mouse Papss2 cDNA was identified by database searching. The 5' end of the cDNA was isolated from a mouse brain cDNA library, constructed from the C57BL/6 strain in the Uni-ZAP XR vector (Stratagene), by amplification from pooled library DNA using a gene specific primer derived from the sequence at locus D19Mit13 (5'-TCTGGCACAAAGAGTTCGTG-3' [SEQ. ID. NO.:19; reverse primer]) and a vector-specific primer. To amplify the entire coding region of Papss2, oligonucleotide primers from the 5' ([a] 5'-GCCAGTTTGTAACCGAGTATTC-3' [SEQ. ID. NO.:20; forward primer]) and 3' ([b] 5'-GCAATTGGATACAGAGCAGC TA-3' [SEQ. ID. NO.:21; reverse primer]) untranslated regions were used. Sequence was determined using the 5' and 3' untranslated region primers as well as primers:
(c) 5'-GACAATGTCCGTCATGGCCTTA-3' (SEQ. ID. NO.:22; forward primer);
(d) 5'-ATTCCCATTGTATTGCCCGTT-3' (SEQ. ID. NO.:23; forward primer);
(e) 5'-AACGGGCAATACAATGGGAAT-3' (SEQ. ID. NO.:24; reverse primer); and
(f) 5'-GATAAAGCTGGTGATGCAAACC-3' (SEQ. ID. NO.:25; reverse primer).

Mutation analysis. To define the human mutation, RNA was purified from a lymphoblastoid cell line from an affected family member. RT-PCR using either the primers from the 5'- and 3'- untranslated regions (primers A and D, above) or internal primers were used to amplify cDNA fragments containing the entire coding region. Control fragments were amplified from human cartilage RNA. Direct sequence analysis of the PCR products using the primers listed above was used to identify the mutation. To confirm the mutation and examine segregation in the Pakistani family, we used HincII digestion of a 108 bp genomic DNA fragment amplified with primers 5'-TGGACCAAGGATGACGATGT-3' (SEQ. ID. NO.:3; forward primer) and 5'-CGGAAAGATGGCAACAATGG-3' (SEQ. ID. NO.:4; reverse primer).

To define the mouse mutation, RNA was purified from frozen spleen from the brachymorphic mouse and a PWK control. (Rusiniak et al. [1996]). The Pappss2 coding region was amplified in two fragments by RT-PCR using primer pair (a) (SEQ. ID. NO. :20; forward primer) plus (g) 5'-CATGGGATGGCGTGAGATAC-3' (SEQ. ID. NO.:26; reverse primer) and primer pair (b) (SEQ. ID. NO.:21; reverse primer) plus (h) 5'-CATAAGCTTTGCTTTGGAAGAGT-3' (SEQ. ID. NO.:27; forward primer), and the sequence was determined using the primers (c)–(f) listed above.

Example 2

Linkage of SEMD Pakistani Type to Markers on Human Chromosome 10

A pooling strategy was used to carry out a genome-wide search for the chromosomal region containing the disease gene in a large inbred Pakistani SEMD family (Ahmad et al., 1998, incorporated by reference). A total of 381 markers were typed, ultimately achieving an average marker spacing of about 10 cM. Individual genotypes for all studied family members were determined for 83 markers that showed differences in allele distributions between the affected and unaffected pools. For all but three of these markers, D10S1432, D10S2470, and D10S677, linkage to the SEMD phenotype could be excluded. Significant linkage was initially obtained for the marker at locus D10S2470, yielding a maximum two-point lod score of 5.44 at a recombination fraction of 0.01.

Saturation genotyping with additional markers from the region confirmed the initial linkage result. Two-point lod scores for all markers are shown in Table 1, with the highest lod score of 5.51 at a recombination fraction of 0.01, obtained for the marker at locus D10S1143.

TABLE 1

Linkage Analysis of Chromosome 10 Markers and SEMD.

| Marker | LOD Score at q = | | | | | | | |
|---|---|---|---|---|---|---|---|---|
| | 0.0 | 0.001 | 0.01 | 0.05 | 0.1 | 0.2 | 0.3 | 0.4 |
| D10S1689 | −0.20 | −0.12 | 0.19 | 0.45 | 0.41 | 0.20 | 0.10 | 0.02 |
| D10S1717 | 2.85 | 3.02 | 3.52 | 3.62 | 3.26 | 2.39 | 1.50 | 0.66 |
| D10S1644 | 4.28 | 4.44 | 4.88 | 4.76 | 4.12 | 2.78 | 1.63 | 0.67 |
| D10S1687 | 4.23 | 4.41 | 4.87 | 4.77 | 4.18 | 2.85 | 1.66 | 0.67 |
| D10S1739 | 2.16 | 2.43 | 3.02 | 3.08 | 2.69 | 1.81 | 1.02 | 0.34 |
| D10S1143 | 4.89 | 5.06 | 5.51 | 5.35 | 4.66 | 3.14 | 1.79 | 0.71 |
| D10S2470 | −∞ | 4.63 | 5.44 | 5.31 | 4.60 | 3.04 | 1.67 | 0.67 |
| D10S1753 | −∞ | −0.57 | 1.02 | 1.80 | 1.74 | 1.20 | 0.66 | 0.20 |

A proximal boundary at locus D10S1689 was established by the haplotypes of three individuals, VI-2, VI-4 and VIII-2. A distal limit at locus D10S2470 was established by a recombination observed in VIII-15. Together, these recombinant events localized the disease gene within a maximum interval of 8.1 cM, flanked on the proximal side by the marker at locus D10S1689 and on the distal side by the marker at locus D10S2470. The genotype of individual VI-7 provided clear evidence of recombination within the 8.1 cM interval. Compatible with the recessive inheritance pattern for the disease, he was homozygous for the marker at only one locus, D10S2470, within the maximum interval. Together with the distal boundary of the larger interval established by the recombination in individual VIII-15, the data showed that the disease gene was contained within the 1.7 cM separating the markers at loci D10S1143 and D10S2470.

FIG. 1 shows a genetic map of the interval containing the SEMD disease gene on human chromosome 10. The darker bar identifies the 8.1 cM maximum interval between loci D10S1689 and D10S2470. The 1.7 cM minimum interval is identified by the darkest bar, between loci D10S1143 and D10S2470. The locations of D10S1432 and D10S677 are not drawn to scale.

Example 3

A novel ATP Sulfurylase/kinase Gene in Mice and Humans

Figure 2:
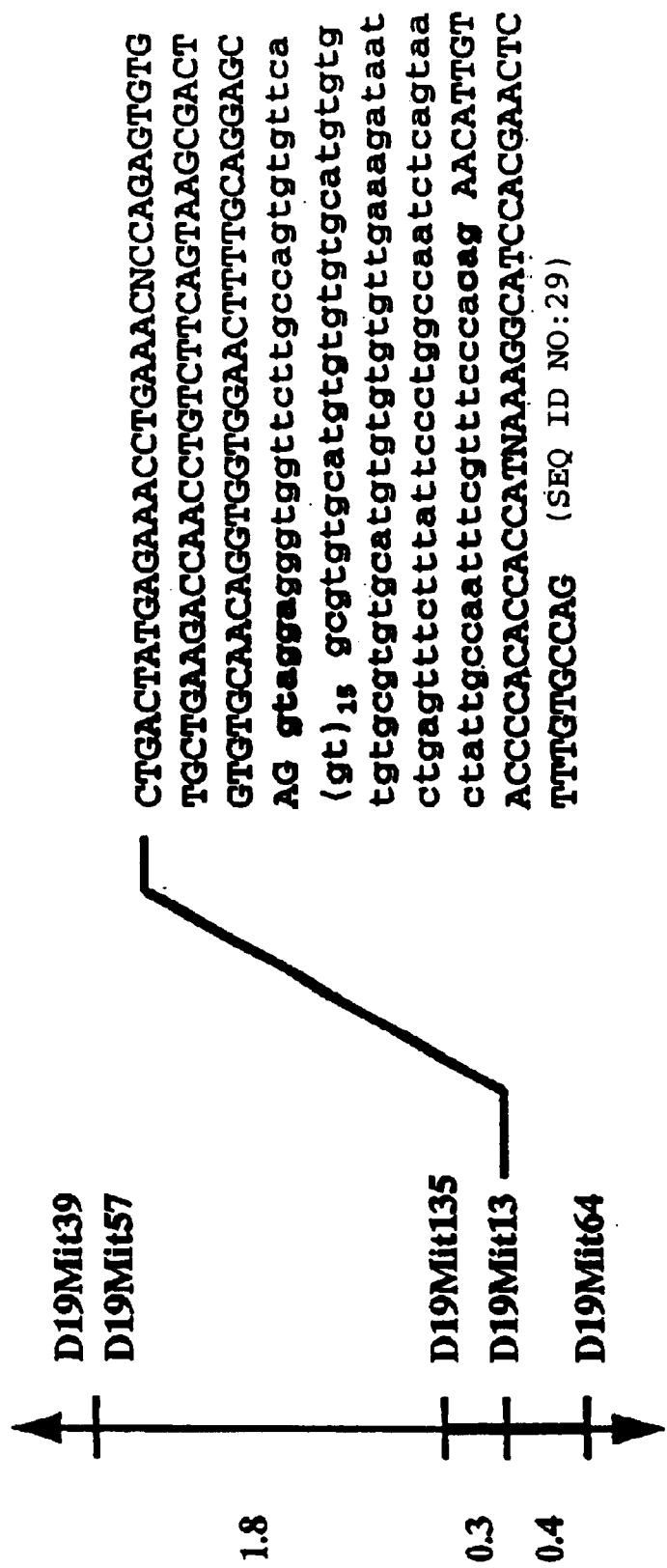
FIG. 2 shows a genetic map of the bm region of mouse chromosome 19. The 0.7 cM interval containing the disease gene and locus D19Mit13 is shown with a darker line; nucleotide sequence of the D19Mit13 locus and flanking sequences are shown in SEQ ID NO:29.

The SEMD interval established by linkage corresponded to chromosomal region 10q23–24, which is syntenic with the region of mouse chromosome 19 to which the recessive mouse skeletal mutant brachymorphic was localized. This regional homology implied that the two phenotypes could be due to mutations in an orthologous pair of genes. Additional recombination mapping using recombinant mice from a large backcross with the brachymorphic mouse showed that only 3 of 25 mice recombinant at the previously defined proximal boundary (Rusiniak, M. E., et al., *Molecular markers near the mouse brachymorphic (bm) gene, which affects connective tissues and bleeding time*, Mamm. Genome 7:98–102 [1996]), the markers at loci D19Mit39 and D19Mit57, were recombinant at locus D19Mit135. The distal limit was not further narrowed by recombination mapping, leaving a total estimated interval of about 0.7 cM, flanked by the markers at loci D19Mit135 and D19Mit64, containing the bm mutation. (FIG. 2).

Figure 4:
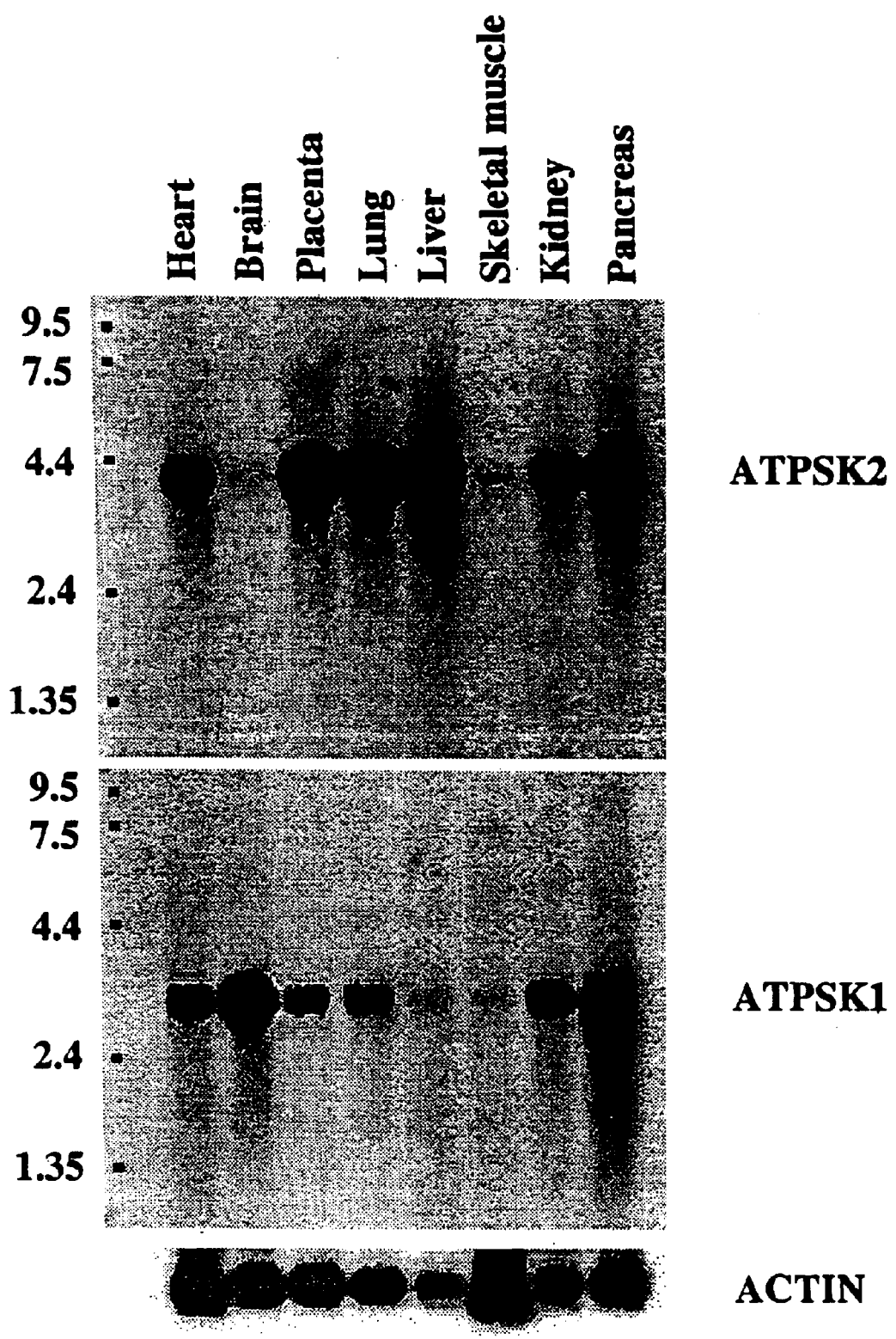
FIG. 4 compares expression of PAPSS1 and PAPSS2 mRNAs with an actin mRNA control in samples from various human tissues, as visualized by Northern hybridization with specific cDNA probes for each.

As in prior genetic mapping studies (Rusiniak et al. [1996]), the marker at locus D19Mit13 was the only marker non-recombinant with the brachymorphic phenotype and, because of the large size of the cross, was therefore expected to be extremely close to the disease gene. A BLAST search using D19Mit13 as the query sequence was carried out to test the hypothesis idea that the marker might be within an intron of the bm gene. Sequences on both sides of the D19Mit13 CA repeat element were about 80% homologous to a human expressed sequence tag (EST), zc38a08.r1, which was distinct from but similar to the known PAPS synthetase gene, Papss1. Comparison of the EST sequence with D19Mit13 revealed that the CA repeat was contained within a 180 base pair intron bordered by consensus splice donor and splice acceptor sequences (data not shown). Further sequential BLAST searches using both the human PAPSS1 and murine Papss1 cDNA sequences, as well as EST sequences derived from each search, identified sets of overlapping ESTs from both species that could be used to assemble partial cDNA sequences. The ESTs were derived from a variety of tissue and cell types, including colon, lung, placenta, aortic endothelium, and fetal heart, suggesting a widely expressed gene. (FIG. 4).

To complete the human cDNA sequence, the nucleotide sequences of PAPSS2 cDNA clones isolated from a human fetal cartilage cDNA library were determined. The reading frame was determined by comparison with the paralogous human PAPSS1 and mouse Papss1 cDNA sequences. At the 5' end, an in-frame ATG codon immediately preceded by a sequence that fit the consensus sequence for translation initiation (Kozak, M., *An analysis of 5'-noncoding sequences from 699 vertebrate messenger RNAs*, Nucleic Acids Res. 15:8125–48 [1987]) was assumed to represent the first translated codon. Conceptual translation of the 615 codon open reading frame predicted a molecular weight of 69,448 Da for the unmodified protein. The coding regions of the human PAPSS2 and PAPSS1 cDNA sequences were 71% identical and the primary translation products were 78% identical. Radiation hybrid mapping localized PAPSS2 at 519 cR on the chromosome 10 map, between loci AFM225YD12 and D10S583, and within the SEMD region defined by linkage.

Sequential BLAST searching and sequence analysis of PCR products from a mouse brain cDNA library was used to complete the coding sequence of the mouse Papss2 cDNA. At the 5' end, there were two in-frame ATG codons, each preceded by a possible consensus sequence for translation initiation. An in-frame stop codon was located just upstream from the first ATG, further supporting the inference that one or both of the two ATG codons represent the site(s) of translation initiation. For purposes of comparison with the human orthologue, we have assumed that the first ATG is used. The open reading frame contains 617 codons and a molecular weight of 69,814 Da was calculated for the encoded protein. The coding regions of the human PAPSS2 and mouse Papss2 genes were 86% identical at the cDNA level and 93% identical at the protein level.

Example 4

A stop Codon in the Human PAPSS2 Gene in the Pakistani SEMD Family

Figure 3:
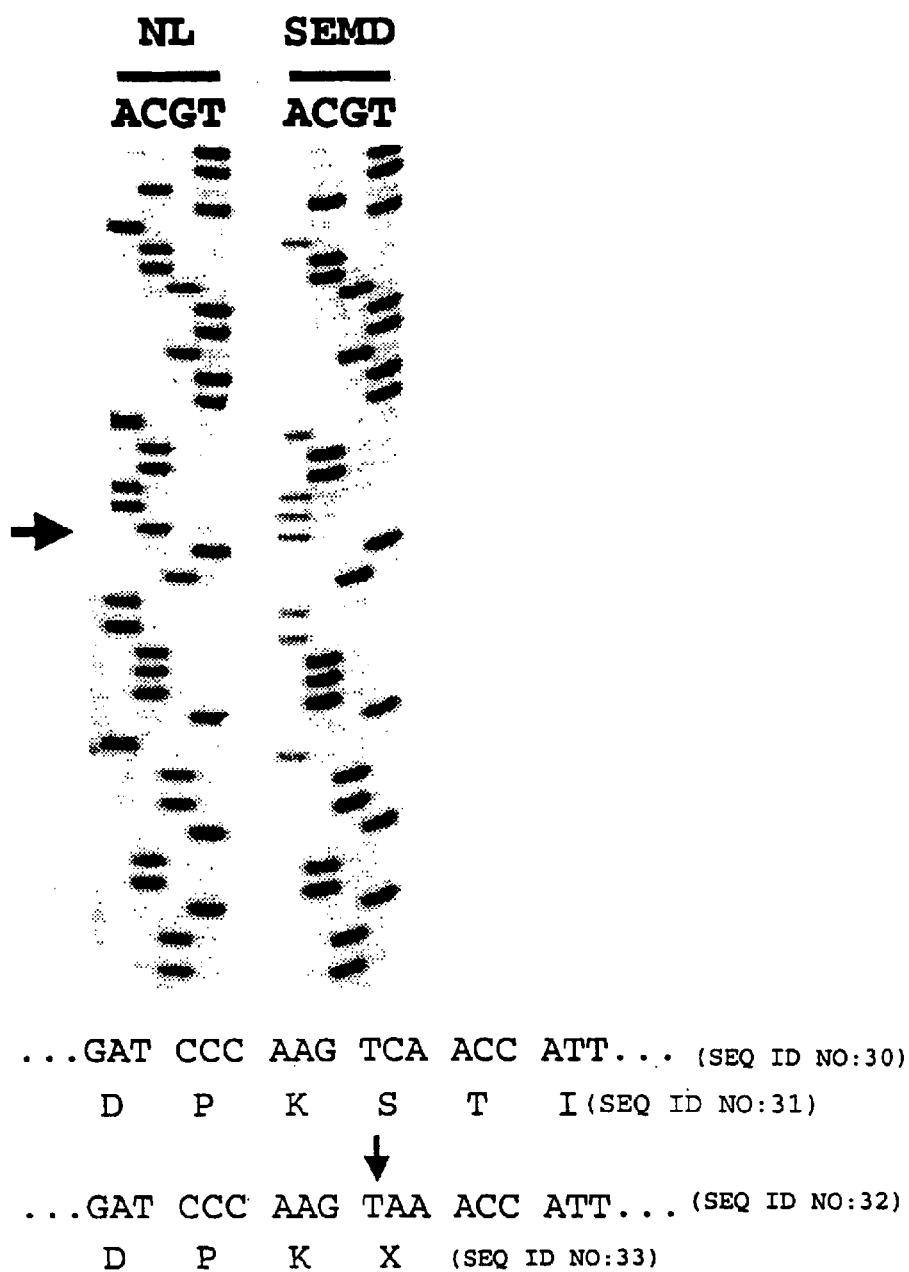
FIG. 3 shows a variant allele of PAPSS2 associated with SEMD Pakistani type. Sequences derived from amplified DNA fragment from an affected family member (SEMD) and from a control (NL) are shown. An arrow at nucleotide +1424 marks the location of a mutation, and the DNA sequence and the implied effect of the mutation on the PAPSS2 protein sequence is summarized below the nucleotide sequence. "Normal" shows nucleotide positions +1414 through +1431 of the PAPSS2 coding sequence (SEQ ID NO:30), with the corresponding amino acid sequence (SEQ ID NO:31) directly underneath. "SEMD" shows nucleotide positions +1414 through +1431 of the PAPSS2 coding sequence containing the mutation at nucleotide position +1424 (SEQ ID NO:32) that produces a TAA stop codon, with the corresponding amino acid sequence (SEQ ID NO:33) directly underneath; "X" indicates truncation of the PAPSS2 protein after amino acid residue 474 of SEQ ID NO:7.

The coding region of the human PAPSS2 cDNA was amplified by RT-PCR using RNA derived from a lymphoblastoid cell line from an affected member of the Pakistani SEMD family. The only sequence change relative to the control fragment, amplified from human fetal cartilage RNA, was a point mutation that predicted a stop codon in place of the serine codon for residue 475 of the protein. (FIG. 3). The mutation thus predicted truncation of the protein from 615 to 474 amino acids. The mutation disrupted a HincII restriction endonuclease cleavage site, and analysis of an amplified genomic DNA fragment containing the site of the mutation by HincII digestion demonstrated cosegregation of the mutation and the phenotype in the family; all affected individuals were homozygous for the mutation, and all obligate carriers (unaffected offspring of affected individuals and unaffected parents of affected individuals) were heterozygous for the mutation (data not shown). None of a panel of 43 DNA samples from individuals of Pakistani origin carried the mutation.

The data presented here demonstrate that a mutation in a novel gene in the sulfate activation pathway results in a human osteochondrodysplasia phenotype. The PAPSS2 mutation characterized in the Pakistani SEMD family introduced a nonsense mutation at the codon for residue 475 of the 615 amino acid protein. It is unknown whether, as has been observed for many other genes (e.g., Willing, M. C., et al., *Premature chain termination is a unifying mechanism for COLIA1 null alleles in osteogenesis imperfecia type I cell strains*, Am. J. Hum. Genet. 59:799–809 [1996]), the nonsense mutation leads to destabilization of the transcript, or if a truncated protein, perhaps retaining partial activity, is synthesized.

Even though the PAPSS2 gene is expressed in a wide variety of tissues (FIG. 4), the mutation produces an exclusively skeletal phenotype. Thus, similar to the disproportionate effect on cartilage of mutations in the gene encoding the widely expressed sulfate transporter DTDST (Hastbacka, J., et al. [1994]; Rossi, A., et al. [1998]), the cartilage-specificity of phenotypic expression is likely the result of the high demand for sulfation of extracellular matrix molecules in cartilage. Differences in levels of expression of the ATPSK1 and PAPSS2 transcripts among different tissues (unpublished data) suggest that this may also influence the tissue-specificity of the phenotype. In cartilage, both PAPSS1 and PAPSS2 transcripts are expressed (unpublished data), but the relative abundances of the proteins in vivo, and their contributions to net PAPS synthesis, are unknown. The milder effect of a mutation in PAPSS2 as compared with DTDST mutations implies that PAPSS1 partially compensates for the PAPSS2 defect by providing a physiologically significant level of PAPS synthesis in cartilage.

Example 5

An Papss2 Missense Mutation in the Brachymorphic Mouse

Complete sequence analysis of the Papss2 coding region from the brachymorphic mouse and the PWK strain used in the backcross identified ten single nucleotide sequence differences between the strains [A at base 295 (A295), G342, G386, C649, G881, C1086, G1239, T1524, G1557, and T1815]. Of these, only two implied sequence differences at the protein level, predicting G79R and K109R substitutions, both within the APS kinase domain of the protein. As the normal mouse strain C57BL/6 was also homozygous for arginine at residue 109, the G79R was the likely pathogenic substitution. A glycine codon is present in the same position among APS kinase domains of eucaryotic Papss genes as well as among APS kinases of bacteria, suggesting it is essential for APS kinase activity.

The conclusion that the G79R Papss2 substitution produces the brachymorphic phenotype is supported by the following evidence. First, the biochemical defect in PAPS synthetase activity measured in brachymorphic cartilage and liver tissue extracts, showing markedly decreased APS kinase activity and a lesser effect on ATP sulfurylase activity, predicts a structural defect affecting the kinase domain of the protein. As the G79R substitution is within the kinase domain, these data are compatible with the biochemical evidence and the hypothesis that the abnormal enzyme does not properly channel APS to the kinase. (Lyle, S., et al., Sulfate-activating enzymes in normal and brachymorphic mice: evidence for a channeling defect, Biochemistry 34:940–45 [1995]). Second, the decrease in Papss activity in liver and cartilage (Schwartz, N. B., et al. [1978]; Sugahara, K. & Schwartz, N. B. [1979]; Sugahara, K. & Schwartz, N. B., *Defect in 3'-phosphoadenosine 5'-phosphosulfate synthesis in brachymorphic mice. II. tissue distribution of the defect*, Arch. Biochem. Biophys. 214:602–09 [1982]) is correlated with the human tissues in which Papss2 is highly expressed (unpublished data). Third, the characterized mutation is the only structural mutation in the coding region that is unique to the brachymorphic mouse. Fourth, the mutation results in substitution for a highly conserved residue among other Papss proteins and APS kinase domains of species from vertebrates to bacteria, suggesting it is essential for kinase activity. Fifth, the phenotype of the brachymorphic mouse and the human SEMD family are substantially similar. Both are recessively inherited dwarfing conditions that affect the spine and long bones. (Lane & Dickie [1968]; Ahmad, M., et al. [1998]). Both phenotypes are evident at birth, but disproportion increases postnatally. Radiographic studies in SEMD Pakistani type (Ahmad, M., et al. [1998]) and histologic analysis of brachymorphic mice (Orkin et al. [1977]) demonstrate that both phenotypes are characterized by a primarily epiphyseal dysplasia with only mild metaphyseal abnormalities. Although brachymorphism is produced by a missense mutation and SEMD by a nonsense mutation, the phenotypic similarity argues that an Papss2 null allele is likely to produce a mouse osteochondrodysplasia phenotype very similar or equivalent to brachymorphic.

The foregoing examples being illustrative but not an exhaustive description of the embodiments of the present invention, the following claims are presented.

We claim:

1. An isolated PAPS synthetase protein comprising a polypeptide having an amino acid sequence of SEQ ID NO:7, or an antibody binding fragment at least 6 amino acids long.

2. A PAPSS2 fusion protein, comprising:

a first PAPSS2 polypeptide segment comprising an amino acid sequence of SEQ ID NO:7 or a gene-specific antibody binding fragment thereof at least 6 amino acids long; and a second predetermined polypeptide segment.

3. The fusion protein of claim 2, wherein the PAPSS2 polypeptide segment is encoded by a nucleic acid segment having a nucleotide sequence of SEQ ID NO:9 or a gene-specific fragment thereof, or by a degenerate sequence of either of these.

4. The PAPSS2 fusion protein of claim 2, wherein the second polypeptide segment is an human immunodeficiency virus TAT protein.

5. The PAPSS2 fusion protein of claim 3, wherein the second polypeptide segment is an human immunodeficiency virus TAT protein.

* * * * *